(12) United States Patent
Sheng et al.

(10) Patent No.: US 11,286,259 B2
(45) Date of Patent: Mar. 29, 2022

(54) CO-CRYSTALS OF RIBOCICLIB AND CO-CRYSTALS OF RIBOCICLIB MONOSUCCINATE, PREPARATION METHOD THEREFOR, COMPOSITIONS THEREOF, AND USES THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Jian Chen, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 66 days.

(21) Appl. No.: 16/651,972

(22) PCT Filed: Sep. 28, 2018

(86) PCT No.: PCT/CN2018/108334
§ 371 (c)(1),
(2) Date: Mar. 27, 2020

(87) PCT Pub. No.: WO2019/062854
PCT Pub. Date: Apr. 4, 2019

(65) Prior Publication Data
US 2020/0262839 A1 Aug. 20, 2020

(30) Foreign Application Priority Data
Sep. 29, 2017 (CN) .......................... 201710904848.0

(51) Int. Cl.
C07D 487/04 (2006.01)
A61K 31/519 (2006.01)
A61P 35/00 (2006.01)
(52) U.S. Cl.
CPC ........ C07D 487/04 (2013.01); C07B 2200/13 (2013.01)
(58) Field of Classification Search
CPC .............. C07D 487/04; C07B 2200/13; A61K 31/519; A61P 35/00
See application file for complete search history.

(56) References Cited

U.S. PATENT DOCUMENTS 10,323,035 B2 * 6/2019 Chen .................... C07D 487/04

FOREIGN PATENT DOCUMENTS

| CN | 101575333 B | 6/2011 |
| CN | 102186856 A | 9/2011 |
| CN | 103201275 A | 7/2013 |
| CN | 105085533 A | 11/2015 |
| CN | 105461702 A | 4/2016 |
| CN | 105753869 A | 7/2016 |
| WO | WO-2019062854 A1 | 4/2019 |

OTHER PUBLICATIONS

International Search Report and Written Opinion for International Application No. PCT/CN2018/108334, State Intellectual Property Office of the P.R. China, China, dated Nov. 30, 2018, 21 pages (with English Translation).

* cited by examiner

Primary Examiner — John M Mauro
(74) Attorney, Agent, or Firm — Sterne, Kessler, Goldstein & Fox P.L.L.C.

(57) ABSTRACT

The present invention relates to co-crystals of ribociclib and co-crystals of ribociclib monosuccinate, comprising the co-crystal of ribociclib and saccharin, the co-crystal of ribociclib and cholic acid, the co-crystal of ribociclib and orotic acid, and the co-crystal of ribociclib monosuccinate and citric acid. Compared with the prior art, the co-crystals have one or more improved properties. The present invention also relates to methods of preparing the co-crystal of ribociclib and saccharin, the co-crystal of ribociclib and cholic acid, the co-crystal of ribociclib and orotic acid, and the co-crystal of ribociclib monosuccinate and citric acid, pharmaceutical compositions, and uses thereof in the preparation of medicines for treating and/or preventing diseases involving one or more symptoms of protein kinase related dysfunctions, cancers, transplant rejection and autoimmune diseases.

27 Claims, 17 Drawing Sheets

CO-CRYSTALS OF RIBOCICLIB AND CO-CRYSTALS OF RIBOCICLIB MONOSUCCINATE, PREPARATION METHOD THEREFOR, COMPOSITIONS THEREOF, AND USES THEREOF

FIELD OF THE INVENTION

The present invention relates to the technical field of crystallization in pharmaceutical chemistry. Specifically, the present application relates to novel co-crystals of ribociclib and co-crystals of ribociclib monosuccinate, their preparation methods therefor and uses thereof as well as the pharmaceutical compositions comprising the new crystal forms.

BACKGROUND

Ribociclib, also known as LEE011, is an orally effective, highly specific cell cycle-dependent kinase (CDK4/6) inhibitor developed by Novartis Pharmaceuticals. Ribociclib, with the trade name of Kisqali, was approved by FDA as a new drug for use in combination with an aromatase inhibitor to treat postmenopausal hormone receptor positive patients and HER-2 negative advanced breast cancer patients.

The chemical name of ribociclib is 7-cyclopentyl-2-(5-piperazin-1-yl-pyridin-2-ylamino)-7H-pyrrolo [2,3-D]pyrimidine-6-carboxylic acid dimethylamide, and its chemical structure is shown in the following formula:

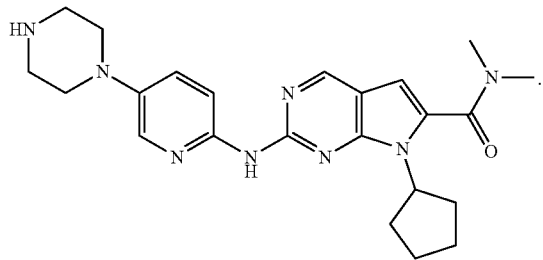 [SMILES: CN(C)C(=O)c1cc2cnc(Nc3ccc(N4CCNCC4)cn3)nc2n1C1CCCC1]

Patent CN102186856B disclosed the compound ribociclib, preparation method, its pharmaceutical composition, and the uses in medicine for treating cancer.

Patent CN105085533A disclosed Form I of ribociclib monosuccinate, its preparation method, pharmaceutical composition, and provided its characterization data. The inventors found from the experimental research that the crystal form has the defect of poor crystal stability in water. Specifically its crystallinity decreased significantly in water and then began to transform to the hydrate crystal form disclosed in CN103201275A. Patent CN105085533A also mentioned two crystal forms of ribociclib monosuccinate disclosed in patent CN103201275A, and found that:

1) the hydrate crystal form has the defect of lower solubility (less than 0.5 mg/mL);

2) the anhydrate crystal form is relatively sensitive to humidity, and easily convert to other crystal forms at high humidity, hence is not suitable for drug development and storage.

Patent CN105753869A disclosed co-crystals of ribociclib and MEK inhibitor, its three co-crystal forms (Form I, Form II, Form III), their preparation methods, pharmaceutical compositions. Form I, Form II and Form III all have an apparent defect of high hygroscopicity, and their weight gain are 2.28%, 5.20%, and 1.12% respectively at a relative humidity of 10% to 80%. This patent also mentioned that Form II could be obtained by heating Form I, and Form II could convert to Form I after being placed for two days at 25(±3°) C/25% RH (relative humidity). This indicates that Form I and Form II are interconvertible, and have poor crystal form controllability, and thus are not suitable for drug development.

The present inventors during research found that the known ribociclib monosuccinate has apparent defects of significant polymorphism, poor stability at high humidity or in water, etc., thus it is not suitable for drug development. The present inventors during research also found that the known co-crystal of ribociclib and MEK inhibitor has the defects of significant polymorphism, poor stability at high temperature, hydrophobicity and poor solubility in water, posing higher requirements for production processes and formulations.

In view of the defects in the prior art, there is a need to develop new solid forms of ribociclib compounds, to improve the bioavailability of pharmaceuticals, to make them easier for industrial production and their post-processing, to obtain better formulations processability, easier to store, and excellent economic value.

SUMMARY OF THE INVENTION

Through a large number of experiments, the present inventors have surprisingly discovered new solid forms of ribociclib compounds, comprising the co-crystal of ribociclib and saccharin, the co-crystal of ribociclib and cholic acid, the co-crystal of ribociclib and orotic acid, the co-crystal of ribociclib monosuccinate and citric acid, and their crystal forms. These co-crystals and crystal forms have unexpectedly good properties, and are more suitable for formulation processing, storage, industrial production, and have better bioavailability. Compared with the known solid forms of ribociclib, co-crystals of ribociclib in present invention have at least one or more superior properties, and achieve unexpected effects. Specific improvements are, for example, higher solubility in water, higher dissolution rate, better stability, lower hygroscopicity, better flowability and favorable processing and handling characteristics, etc. Preferably, the new solid forms in present invention have higher solubility and stability.

According to an objective of the present invention, one of the technical problems to be solved by the present invention is to provide a co-crystal of ribociclib and saccharin, and preparation methods thereof.

The co-crystal of ribociclib and saccharin provide by the present invention is the compound of the following formula (I), formed by ribociclib and saccharin at a molar ratio of 1:1.

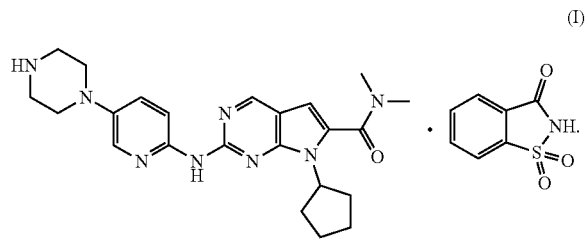

A method of preparing the co-crystal of ribociclib and saccharin comprises a reaction of ribociclib with one equivalent to two equivalents of saccharin, preferably a reaction in an organic solvent solution or in a mixed organic solvent solution. The organic solvent is a solvent capable of dissolving ribociclib or saccharin.

According to an objective of the present invention, the second technical problem to be solved by the invention is to provide co-crystal forms of ribociclib and saccharin, and preparation methods thereof.

The co-crystal of ribociclib and saccharin is essentially crystalline, preferably, crystal forms of an anhydrate, a hydrate or a non-solvate.

Preferably, the X-ray powder diffraction pattern of the co-crystal form has the following characteristic peaks at $2\theta$ values of $8.4°\pm0.2°$, $10.2°\pm0.2°$, $12.7°\pm0.2°$, $17.7°\pm0.2°$, $21.0°\pm0.2°$ and $22.7°\pm0.2°$.

More preferably, the X-ray powder diffraction pattern of the co-crystal form has the following characteristic peaks at $2\theta$ values of $10.8°\pm0.2°$, $13.7°\pm0.2°$, $14.0°\pm0.2°$, $18.4°\pm0.2°$, $19.0°\pm0.2°$ and $20.5°\pm0.2°$.

Further preferably, the X-ray powder diffraction pattern of the co-crystal form has the following characteristic peaks at $2\theta$ values of $11.0°\pm0.2°$, $14.7°\pm0.2°$, $16.8°\pm0.2°$, $17.2°\pm0.2°$, $19.8°\pm0.2°$ and $22.0°\pm0.2°$.

Non-restrictively, the XRPD pattern of the co-crystal is essentially shown in FIG. 4.

In one specific embodiment of the present invention, the X-ray powder diffraction pattern of the co-crystal has the following characteristic peaks at $2\theta$ values of $8.4°\pm0.2°$, $10.2°\pm0.2°$, $10.8°\pm0.2°$, $11.0°\pm0.2°$, $12.7°\pm0.2°$, $13.7°\pm0.2°$, $14.0°\pm0.2°$, $14.7°\pm0.2°$, $16.8°\pm0.2°$, $17.2°\pm0.2°$, $17.7°\pm0.2°$, $18.4°\pm0.2°$, $18.7°\pm0.2°$, $19.0°\pm0.2°$, $19.1°\pm0.2°$, $19.8°\pm0.2°$, $20.5°\pm0.2°$, $21.0°\pm0.2°$, $22.0°\pm0.2°$, $22.7°\pm0.2°$, $24.1°\pm0.2°$, $25.8°\pm0.2°$ and $26.4°\pm0.2°$.

Non-restrictively, the XRPD pattern of the co-crystal is essentially shown in FIG. 5, the TGA thermogram is essentially shown in FIG. 7, the DSC thermogram is essentially shown in FIG. 8, the isothermal adsorption curve is essentially shown in FIG. 9.

In another embodiment of the present invention, the X-ray powder diffraction pattern of the co-crystal has the following characteristic peaks at $2\theta$ values of $6.3°\pm0.2°$, $8.4°\pm0.2°$, $10.2°\pm0.2°$, $10.8°\pm0.2°$, $11.0°\pm0.2°$, $12.7°\pm0.2°$, $13.7°\pm0.2°$, $14.0°\pm0.2°$, $14.7°\pm0.2°$, $16.8°\pm0.2°$, $17.2°\pm0.2°$, $17.7°\pm0.2°$, $18.4°\pm0.2°$, $19.0°\pm0.2°$, $19.8°\pm0.2°$, $20.5°\pm0.2°$, $21.0°\pm0.2°$, $22.0°\pm0.2°$, $22.7°\pm0.2°$, $25.5°\pm0.2°$, $32.0°\pm0.2°$ and $38.5°\pm0.2°$.

Non-restrictively, the XRPD pattern of the co-crystal form is essentially shown in FIG. 6.

Non-restrictively, the single crystal of the co-crystal of ribociclib and saccharin, measured at 106K, belongs to the monoclinic system with a space group of $P2_1/c$, and has the following single crystal cell parameters: the axis length a=13.6 Å$\pm$0.2 Å, b=15.8 Å$\pm$0.2 Å, c=13.9 Å$\pm$0.2; the dihedral angle $\alpha$=90°, $\beta$=93.4°$\pm$0.2°, $\gamma$=90°.

According to an objective of the present invention, the present invention provides a method of preparing the co-crystal form of ribociclib and saccharin, comprising any one of the following methods:

mixing ribociclib, saccharin and a solvent, then crystallizing to obtain the co-crystal of ribociclib and saccharin; wherein the solvent is selected from the group consisting of a $C_1$ to $C_4$ alcohol, a $C_4$ to $C_5$ ester, an alkane, a $C_4$ to $C_6$ ether, a $C_3$ to $C_4$ ketone, acetonitrile, dimethylsulfoxide, water, and any mixture thereof;

(1) The crystallization method is a volatilization method;
Preferably, the molar ratio of ribociclib to saccharin is 1:1;
Preferably, the solvent is selected from the group consisting of methanol, ethanol, acetone, acetonitrile, ethyl acetate, water and any mixture thereof;
Preferably, the operation is performed at 10° C. to 40° C., more preferably at room temperature;
Preferably, the mass-volume ratio of ribociclib to the solvent ranges from 1 mg/mL to 25 mg/mL;

(2) The crystallization method is a crystal slurry method;
Preferably, the molar ratio of ribociclib to saccharin ranges from 1:1 to 1:2;
Preferably, the solvent is selected from the group consisting of methanol, ethanol, isopropanol, acetonitrile, tetrahydrofuran, water, and any mixture thereof;
Preferably, the operation is performed at 10° C. to 40° C., more preferably at room temperature;
Preferably, the duration for reaction ranges from 8 hours to 72 hours; more preferably from 24 hours to 72 hours;
Preferably, the mass-volume ratio of ribociclib to the solvent ranges from 25 mg/mL to 50 mg/mL;

(3) The crystallization method is a solid grinding method;
Preferably, the molar ratio of ribociclib to saccharin ranges from 1:0.5 to 1:2;
Preferably, the solvent is selected from the group consisting of methanol, acetone, tetrahydrofuran, dichloromethane, water, and any mixture thereof;
Preferably, the mass-volume ratio of the mixture to the solvent ranges from 50 mg/mL to 100 mg/mL;
Preferably, the operation is performed at 10° C. to 40° C., more preferably at room temperature;

(4) The crystallization method is a cooling crystallization method; wherein the starting point temperature ranges from 50° C. to 60° C.;
Preferably, the molar ratio of ribociclib to saccharin ranges from 1:1 to 1:2;
Preferably, the solvent is selected from the group consisting of methanol, ethanol, acetone, 1,4-dioxane, water, and any mixture thereof;
Preferably, the ending point temperature ranges from 0° C. to 30° C., more preferably 4° C.;
Preferably, the cooling rate ranges from 5 to 10° C./hour;
Preferably, the mass-volume ratio of ribociclib to the solvent ranges from 10 mg/mL to 50 mg/mL;

The co-crystal of ribociclib and saccharin has the following beneficial effects:

(1) The known co-crystals of ribociclib and MEK has three crystal forms, while the co-crystal form of ribociclib and saccharin in the present invention is unitary, and has high processablility.

(2) The known three forms of the co-crystal of ribociclib and MEK all have higher hygroscopicity, and their weight gain are shown to be 2.28%, 5.20%, and 1.12% respectively at a relative humidity of 10% to 80%. The co-crystal of ribociclib and saccharin in present invention has lower hygroscopicity, and its weight gain is 0.45% at a relative humidity of 10% to 80%.

(3) According to Comparative Example 1, the co-crystal Form III of ribociclib and MEK cannot maintain its original crystal form after being placed for 24 hours at 80° C. The co-crystal form of ribociclib and saccharin in the present invention remains unchanged after being placed for 24 hours at 80° C. It indicates that the co-crystal of ribociclib and saccharin in the present invention has higher crystal stability.

(4) According to Comparative Example 2, the solubility in water at 25° C. of the co-crystal of ribociclib and saccharin is higher than the known co-crystal Form III of ribociclib and MEK. It indicates that co-crystal of ribociclib and saccharin in the present invention has better solubility, thus has better bioavailability.

(5) Patent CN105085533A also mentioned that the anhydrate crystal form of ribociclib monosuccinate disclosed in patent CN103201275A is sensitive to humidity, and easily converts to other crystal forms at high humidity. The co-crystal form of ribociclib and saccharin in the present invention remains unchanged and has significant stability at high humidity.

The appearance, XRPD and melting point of the co-crystal of ribociclib and saccharin remain unchanged after being placed in a desiccator for 4 months at room temperature and relative humidity of 10% to 90%. It indicates that the co-crystal of ribociclib and saccharin has good storage stability, avoiding or reducing the quality, safety and stability related problems, such as content uniformity and impurity issues during drug manufacturing and/or storage of the active ingredient and the formulations containing the co-crystal of ribociclib and saccharin, and also avoiding the use of special and expensive packaging. On the other hand, the co-crystal of ribociclib and MEK has two active ingredients at a fixed ratio, which could not be flexibly adjusted; and if the ratio of active ingredients is altered, it is difficult to maintain the co-crystal status and its efficacy. This is not the case for the co-crystal ribociclib and saccharin, which contains only the active ingredient of ribociclib.

The third technical problem to be solved by the present invention is to provide a co-crystal of ribociclib and cholic acid.

The co-crystal of ribociclib and cholic acid provide by the present invention has the following formula (II); preferably a co-crystal formed by ribociclib and cholic acid at a molar ratio of 1:1.

A method of preparing the co-crystal of ribociclib and cholic acid comprises a reaction of ribociclib with one equivalent to two equivalents of cholic acid, preferably a reaction in an organic solvent solution or in a mixed organic solvent solution. The organic solvent is a solvent capable of dissolving ribociclib or cholic acid.

According to an objective of the present invention, the fourth technical problem to be solved by the invention is to provide co-crystal forms of ribociclib and cholic acid.

The co-crystal of ribociclib and cholic acid basically is crystalline, preferably, crystal forms of an anhydrate, a hydrate or a non-solvate. The crystal forms are the co-crystal Form I and Form II of ribociclib and cholic acid.

Non-restrictively, the co-crystal Form I of ribociclib and cholic acid, measured at 100K, belongs to the monoclinic system with a space group of P1, and has the following single crystal cell parameters: the axis length a=7.6±0.2 Å, b=16.9±0.2 Å, c=20.1±0.2 Å; the dihedral angle is α=98.8±0.2°, β=95.3±0.2°, γ=90.4±0.2°.

Preferably, the X-ray powder diffraction pattern of the co-crystal Form I of ribociclib and cholic acid has the following one or more characteristic peaks at 2θ values of 4.6±0.2°, 9.1±0.2°, 10.9±0.2° and 15.9±0.2°.

More preferably, the X-ray powder diffraction pattern of the co-crystal Form I of ribociclib and cholic acid has the following one or more characteristic peaks at 2θ values of 5.3°±0.2°, 12.1°±0.2°, 17.3°±0.2°, 19.5°±0.2°, and 23.5°±0.2°.

Further preferably, the X-ray powder diffraction pattern of the co-crystal Form I of ribociclib and cholic acid has the following one or more characteristic peaks at 2θ values of 7.6°±0.2°, 16.9°±0.2°, 20.1°±0.2° and 32.0°±0.2°.

Non-restrictively, the XRPD pattern of the co-crystal Form I of ribociclib and cholic acid is essentially shown in FIG. 11, the TGA thermogram is essentially shown in FIG. 12, the DSC thermogram is essentially shown in FIG. 13, and the $^1$HNMR spectrum is essential shown in FIG. 14.

The X-ray powder diffraction pattern of the co-crystal Form II of ribociclib and cholic acid has the following one or more characteristic peaks at 2θ values of 4.6°±0.2°, 9.4°±0.2°, 11.1°±0.2°, 12.3°±0.2°, 15.0°±0.2°, 15.2°±0.2°, 16.2°±0.2°, 16.6°±0.2°, 17.6°±0.2°, 18.9°±0.2°, 20.3±0.2° and 20.6°±0.2°.

Non-restrictively, the XRPD pattern of the co-crystal Form II of ribociclib and cholic acid is essentially shown in FIG. 15.

The co-crystal Form I of ribociclib and cholic acid has the following beneficial effects:

(1) According to Comparative Example 1, the solubility of the co-crystal Form I of ribociclib and cholic acid in water at 25° C. is 30 to 50 times higher than the co-crystal Form III of ribociclib and MEK. It indicates that co-crystal Form I of ribociclib and cholic acid in the present invention has better solubility and better bioavailability.

(2) The melting point of the co-crystal Form I of ribociclib and cholic acid is 226° C., and is higher than that of the co-crystal Form III of ribociclib and MEK (about 165° C.). It incadites that the co-crystal Form I of ribociclib and cholic acid in the present invention has better thermal stability.

(3) Patent CN105085533A also mentioned that the anhydrate crystal form of ribociclib monosuccinate disclosed in patent CN103201275A is sensitive to humidity, and easily converts to other crystal forms at high humidity. The co-crystal form of ribociclib and cholic acid in the present invention remains unchanged and has significant stability at high humidity.

The appearance, XRPD and melting point of the co-crystal Form I of ribociclib and cholic acid remain unchanged after being placed in a desiccator for 4 months at room temperature and relative humidity of 10% to 90%. It indicates that the co-crystal Form I of ribociclib and cholic acid has good storage stability, which can avoid or reduce the quality, safety and stability related problems, such as content uniformity and impurity issues during drug manufacturing and/or storage of the pharmaceutically active ingredient and the formulations containing the co-crystal Form I of ribociclib and cholic acid, and also avoiding the use of special and expensive packaging.

The fifth technical problem to be solved by the present invention is to provide the co-crystal of ribociclib and orotic acid, and preparation methods thereof.

The co-crystal of ribociclib and orotic acid provide by the present invention has the following formula (III); preferably a co-crystal formed by ribociclib and orotic acid at a molar ratio of 1:1.

A method of preparing the co-crystal of ribociclib and orotic acid comprises a reaction of ribociclib with one equivalent to two equivalents of orotic acid, preferably a reaction in an organic solvent solution or in a mixed organic solvent solution. The organic solvent is a solvent capable of dissolving ribociclib or orotic acid.

According to an objective of the present invention, the sixth technical problem to be solved by the invention is to provide co-crystal forms of ribociclib and orotic acid.

The co-crystal of ribociclib and orotic acid is essentially crystalline, preferably, crystal forms of an anhydrate, a hydrate or a non-solvate. The crystal forms are the co-crystal Form I and the co-crystal Form II of ribociclib and orotic acid.

Preferably, the X-ray powder diffraction pattern of the co-crystal Form I of ribociclib and orotic acid has the following one or more characteristic peaks at 2θ values of 5.7±0.2°, 16.8±0.2°, 22.2±0.2°, 24.1±0.2°.

More preferably, the X-ray powder diffraction pattern of the co-crystal Form I of ribociclib and orotic acid has the following one or more characteristic peaks at 2θ values of 11.3°±0.2°, 11.9°±0.2°, 15.5°±0.2°, 16.1°±0.2° and 27.0°±0.2°.

Further preferably, the X-ray powder diffraction pattern of the co-crystal Form I of ribociclib and orotic acid has the following one or more characteristic peaks at 2θ values of 8.1°±0.2°, 11.5°±0.2°, 17.4°±0.2°, and 19.0°±0.2°.

Non-restrictively, the XRPD pattern of the co-crystal Form I of ribociclib and orotic acid is essentially shown in FIG. 16, the TGA thermogram is essentially shown in FIG. 17, the DSC thermogram is essentially shown in FIG. 18, and the $^1$HNMR spectrum is essentially shown in FIG. 19.

The X-ray powder diffraction pattern of the co-crystal Form II of ribociclib and orotic acid has the following one or more characteristic peaks at 2θ values of 6.6°±0.2°, 6.9°±0.2°, 8.9°±0.2°, 14.1°±0.2°, 14.6°±0.2°, 16.8°±0.2°, 17.9°±0.2°, 18.5°±0.2°, 20.4°±0.2°, 22.7°±0.2°, 23.4°±0.2°, 26.6±0.2°, 27.0°±0.2°, 29.2°±0.2° and 31.6±0.2°.

Non-restrictively, the XRPD pattern of the co-crystal Form II of ribociclib and orotic acid is essentially shown in FIG. 20.

The co-crystal Form I of ribociclib and orotic acid has the following beneficial effects:

(1) According to Comparative Example 1, the solubility of co-crystal Form I of ribociclib and orotic acid in water at 25° C. is 30 to 50 times higher than that of the co-crystal Form III of ribociclib and MEK. It indicates that the co-crystal Form I of ribociclib and orotic acid in the present invention has better solubility and better bioavailability.

(2) The melting point of the co-crystal Form I of ribociclib and orotic acid is 272° C., and is higher than that of the co-crystal Form III of ribociclib and MEK (about 165° C.). It indicates that the co-crystal Form I of ribociclib and orotic acid has better thermal stability.

(3) Patent CN105085533A also mentioned that the anhydrate crystal form of ribociclib monosuccinate disclosed in patent CN103201275A is sensitive to humidity, and easily converts to other crystal forms at high humidity. The co-crystal form of ribociclib and orotic acid in the present invention remains unchanged and has significant stability at high humidity.

The appearance, XRPD and melting points of the co-crystal Form I of ribociclib and orotic acid remain unchanged after being placed in a desiccator for 4 months at room temperature and relative humidity of 10% to 90%. It indicates that the co-crystal Form I of ribociclib and orotic acid has good storage stability, and can avoid or reduce the quality, safety and stability related problems, such content uniformity and impurity issues during drug manufacturing and/or storage of the pharmaceutically active ingredient and the formulations containing the co-crystal Form I of ribociclib and orotic acid, and also avoid the use of special and expensive packaging.

According to an objective of the present invention, the seventh technical problem to be solved by the present invention is to provide methods of preparing the co-crystal forms of ribociclib and cholic acid, and the co-crystal forms of ribociclib and orotic acid.

The preparation method of the co-crystal Form I of ribociclib and cholic acid, and co-crystal Form I of ribociclib and orotic acid, is selected from any one of the following methods:

Mixing ribociclib, cholic acid or orotic acid, and a solvent to react, after reaction removing solvent to obtain the co-crystals, wherein the solvent is selected from the group consisting of an alcohol, an ester, a ketone, an alkane (including a haloalkane), an ether (including a cyclic ether), acetonitrile, dimethylsulfoxide, water, and any mixture thereof;

(1) The crystallization method is a slurry method;
   Preferably, the solvent is selected from the group consisting of methanol, ethanol, acetone, acetonitrile, tetrahydrofuran, water, and any mixture thereof;
   Preferably, the molar ratio of ribociclib to the corresponding acid ranges from 1:1 to 1:2;
   Preferably, the operation is performed at 10° C. to 40° C., more preferably at room temperature;
   Preferably, the duration for crystallization ranges from 8 hours to 72 hours; more preferably from 24 hours to 72 hours;
   Preferably, the mass-volume ratio of ribociclib to the solvent ranges from 10 mg/mL to 50 mg/mL;
   Preferably, the mass-volume ratio of the corresponding acid to the solvent ranges from 10 mg/mL to 65 mg/mL;

(2) The crystallization method is a solid grinding method;
   Preferably, the solvent is selected from the group consisting of methanol, ethanol, tetrahydrofuran, dichloromethane, water, and any mixture thereof;
   Preferably, the mass-volume ratio of the mixture to the solvent ranges from 27 mg/mL to 100 mg/mL;
   Preferably, the operation is performed at 10° C. to 40° C., more preferably at room temperature;

(3) The crystallization method is a volatilization method;
   Preferably, the solvent is selected from the group consisting of methanol, ethanol, isopropanol, ethyl acetate, acetonitrile, water, and any mixture thereof;
   Preferably, the operation is performed at 10° C. to 40° C., more preferably at room temperature;
   Preferably, the mass-volume ratio of the mixture to the solvent ranges from 3 mg/mL to 20 mg/mL;

(4) The crystallization method is a cooling crystallization method;
   Preferably, the molar ratio of ribociclib to the corresponding acid ranges from 1:1 to 1:2;
   Preferably, the solvent is selected from the group consisting of methanol, ethanol, acetone, 1,4-dioxane, water, and any mixture thereof;
   Preferably, the crystallization temperature ranges from 0° C. to 30° C., more preferably 4° C.;
   Preferably, the cooling rate ranges from 5 to 10° C./hour;
   Preferably, the mass-volume ratio of the mixture to the solvent ranges from 19 mg/mL to 60 mg/mL.

The co-crystal Form II of ribociclib and cholic acid, and the co-crystal Form II of ribociclib and orotic acid are prepared as follows: heating the co-crystal Form I of ribociclib and cholic acid, or the co-crystal Form I of ribociclib and orotic acid to 60 to 100° C. at a rate of 5 to 10° C./min, then maintaining at that temperature for 10 to 30 minutes.

The eighth technical problem to be solved by the present invention is to provide the co-crystal of ribociclib monosuccinate, and preparation methods thereof.

The co-crystal of ribociclib monosuccinate and citric acid provided by the present invention is the compound of the following formula (IV), formed by ribociclib monosuccinate and citric acid at a molar ratio of 1:1.

A method of preparing the co-crystal of ribociclib monosuccinate and citric acid comprises a reaction of ribociclib monosuccinate with one equivalent to two equivalents of citric acid, preferably a reaction in an organic solvent solution or in a mixed organic solvent solution. The organic solvent is a solvent capable of dissolving ribociclib monosuccinate or citric acid.

According to an objective of the present invention, the ninth technical problem to be solved by the present invention is to provide co-crystal forms of ribociclib monosuccinate and citric acid, and preparation methods thereof.

The co-crystal of ribociclib monosuccinate and citric acid basically is crystalline, preferably, crystal forms of an anhydrate, a hydrate or a non-solvate.

Preferably, the X-ray powder diffraction pattern of the co-crystal form of ribociclib monosuccinate and citric acid has the following one or more characteristic peaks at 2θ values of 8.4°±0.2°, 10.6°±0.2°, 12.9°±0.2° and 17.4°±0.2°.

More preferably, the X-ray powder diffraction pattern of the co-crystal form of ribociclib monosuccinate and citric acid has the following one or more characteristic peaks at 2θ values of 4.3°±0.2°, 15.1°±0.2°, 18.8°±0.2°, 20.7°±0.2° and 22.2±0.2°.

Further preferably, the X-ray powder diffraction pattern of the co-crystal form of ribociclib monosuccinate and citric acid has the following one or more characteristic peaks at 2θ values of 12.3°±0.2°, 14.0°±0.2°, 16.8°±0.2°, 22.6°±0.2° and 23.8°±0.2°.

More further preferably, the X-ray powder diffraction pattern of the co-crystal form of ribociclib monosuccinate and citric acid has the following one or more characteristic peaks at 2θ values of 15.4°±0.2°, 15.9°±0.2°, 19.6°±0.2°, 21.6°±0.2° and 23.2°±0.2°.

Non-restrictively, the XRPD pattern of the co-crystal form of ribociclib monosuccinate and citric acid is essentially shown in FIG. 21.

In one embodiment of the present invention, the X-ray powder diffraction pattern of the co-crystal of ribociclib monosuccinate and citric acid has the following one or more characteristic peaks at 2θ values of 4.3°±0.2, 8.4°±0.2, 10.6°±0.2, 12.3°±0.2, 12.9°±0.2, 14.0°±0.2, 15.1°±0.2, 15.4°±0.2, 15.9°±0.2, 16.8°±0.2°, 17.4°±0.2, 18.8°±0.2, 18.9°±0.2, 19.2°±0.2, 9.6°±0.2, 120.7°±0.2, 21.2°±0.2, 21.6°±0.2, 22.2±0.2, 22.6°±0.2, 23.2°±0.2, 23.8°±0.2 and 28.6°±0.2.

Non-restrictively, the XRPD pattern of the co-crystal is essentially shown in FIGS. 21-22, the TGA thermogram of is essentially shown in FIG. 23, the DSC thermogram is essentially shown in FIG. 24, and the $^1$HNMR spectrum is essentially shown in FIG. 25.

According to an objective of the present invention, the present invention provides a method of preparing the co-crystal form of ribociclib monosuccinate and citric acid, comprising any one of the following methods:

Mixing ribociclib monosuccinate, citric acid and a solvent to react, after reaction removing solvent to obtain the co-crystal of ribociclib monosuccinate and citric acid; wherein the solvent is selected from the group consisting of an alcohol, an ester, a ketone, an alkane (including a haloalkane), an ether (including a cyclic ether), acetonitrile, dimethylsulfoxide, water, and any mixture thereof;

(1) The crystallization method is a volatilization method;
  Preferably, the molar ratio of ribociclib monosuccinate to citric acid is 1:1.
  Preferably, the solvent is selected from the group consisting of methanol, ethanol, isopropanol, tetrahydrofuran, water, and any mixture thereof;
  Preferably, the operation is performed at 10° C. to 40° C., more preferably at room temperature;
  Preferably, the mass-volume ratio of ribociclib monosuccinate to the solvent ranges from 1 mg/mL to 35 mg/mL;

(2) The crystallization method is a slurry method;
  Preferably, the molar ratio of ribociclib monosuccinate to citric acid ranges from 1:1 to 1:2;
  Preferably, the solvent is selected from the group consisting of methanol, ethanol, acetone, ethyl acetate, water, tetrahydrofuran, and any mixture thereof;
  Preferably, the operation is performed at 10° C. to 40° C., more preferably at room temperature;
  Preferably, the duration for reaction ranges from 8 hours to 72 hours; more preferably from 24 hours to 72 hours;
  Preferably, the mass-volume ratio of ribociclib monosuccinate to the solvent ranges from 10 mg/mL to 50 mg/mL;

(3) The crystallization method is a solid grinding method;
  Preferably, the molar ratio of ribociclib monosuccinate to citric acid ranges from 1:0.5 to 1:2;
  Preferably, the solvent is selected from the group consisting of methanol, acetone, tetrahydrofuran, ethyl acetate, dichloromethane, water, and any mixture thereof; Preferably, the mass-volume ratio of the mixture to the solvent ranges from 50 mg/mL to 100 mg/mL;
  Preferably, the operation is performed at 10° C. to 40° C., more preferably at room temperature;

(4) The crystallization method is a cooling crystallization method; wherein the starting point temperature is 50° C. to 60° C.;
  Preferably, the molar ratio of ribociclib monosuccinate to citric acid is from 1:1 to 1:2;
  Preferably, the solvent is selected from the group consisting of methanol, ethanol, acetone, water, tetrahydrofuran, dimethyl sulfoxide, and any mixture thereof
  Preferably, the ending point temperature ranges from 0° C. to 30° C., more preferably 4° C.;
  Preferably, the cooling rate ranges from 5 to 10° C./hour;
  Preferably, the mass-volume ratio of ribociclib monosuccinate to the solvent ranges from 10 mg/mL to 50 mg/mL;

Compared with the co-crystal Form III of ribociclib and MEK in the prior art, the co-crystal of ribociclib monosuccinate and citric acid in the present invention has the following beneficial properties:

(1) The known co-crystal of ribociclib and MEK has three crystal forms, and the known ribociclib monosuccinate has three crystal forms. While the co-crystal form of ribociclib monosuccinate and citric acid is unitary, and has high process controllability.

(2) According to Comparative Example 1, the co-crystal Form III of ribociclib and MEK cannot maintain its original crystal form after being placed for 24 hours at 80° C. The co-crystal form of ribociclib monosuccinate and citric acid in the present invention remains unchanged after being placed for 24 hours at 80° C. It indicates that the co-crystal of ribociclib monosuccinate and citric acid in the present invention has higher crystal stability.

(3) According to Comparative Example 2, the solubility of the co-crystal of ribociclib monosuccinate and citric acid in water at 25° C. is 10000 to 20000 times higher than that of the co-crystal Form III of ribociclib and MEK. It indicates that the co-crystal of ribociclib monosuccinate and citric acid in the present invention have better solubility and better bioavailability.

(4) According to Comparative Example 3, the known crystal Form I of ribociclib monosuccinate cannot maintain its original crystal form after having been stirred in water at 25° C. for 24 hours, while the co-crystal form of ribociclib monosuccinate and citric acid in the present invention remains unchanged after having been stirred in water at 25° C. for 24 hours. It indicates that co-crystal form of ribociclib monosuccinate and citric acid has better higher stability in water, thus has better formulation processability.

(5) Patent CN105085533A also mentioned that the anhydrate crystal form of ribociclib monosuccinate disclosed in patent CN103201275A is sensitive to humidity, and easily converts to other crystal forms at high humidity. The co-crystal form of ribociclib monosuccinate and citric acid in the present invention remains unchanged and has significant stability at high humidity.

The appearance, XRPD and melting point of the co-crystal of ribociclib monosuccinate and citric acid remain unchanged after being placed in a desiccator for 4 months at room temperature and relative humidity of 10% to 90%. It indicates that the co-crystal of ribociclib monosuccinate and citric acid has good storage stability, and can avoid or reduce the quality, safety and stability related problems, such as content uniformity and impurity issues during drug manufacturing and/or storage of the pharmaceutically active ingredient and the formulations containing the co-crystal of ribociclib monosuccinate and citric acid, and also avoiding the use of special and expensive packaging.

In preparation methods of co-crystals of ribociclib or the co-crystal of ribociclib monosuccinate in the present invention:

Unless particularly specified, "Room temperature" refers to a temperature between 10° C. and 30° C.

The "cyclic ether" can be tetrahydrofuran or 1,4-dioxane.

The "haloalkane" can be dichloromethane or chloroform.

The "stirring" can be accomplished with the routine methods in the field, such as magnetic stirring, mechanical stirring, and the stirring speed ranges from 50 to 1800 r/min, preferably from 300 to 900 r/min.

The "removing solvent" can be accomplished with the routine methods in the field, such as filtering or centrifugation. The preferred method is filtration under reduced pressure, which is generally carried out by suction at a pressure of less than atmospheric pressure at room temperature, preferably at a pressure of less than 0.09 MPa. The specific operation of "centrifugation" is as follows: the sample to be separated is placed in a centrifuge tube and centrifuged at a rate of 6000 rpm until all the solids are settled to the bottom of the centrifuge tube.

"Drying" can be accomplished with the routine methods in the field, such as drying at room temperature, blast drying and drying under reduced pressure. The pressure can be reduced pressure or atmospheric pressure, preferably less than 0.09 MPa. Drying instruments and methods are unrestricted, and may be fume hood, blast oven, spray drying fluidized bed drying or vacuum oven; drying is performed under reduced pressure or atmospheric pressure, preferably less than 0.09 MPa.

The "co-crystal" form in the present invention means that the compound is confirmed by the X-ray powder diffraction pattern characterization shown and has a unique and ordered molecular arrangement or configuration within the crystal lattice. It is well known to those skilled in the art that the experimental error depends on the instrument conditions, sample preparation and sample purity. The 2θ angle of the peaks in the XRD pattern usually varies slightly depending on the instrument and sample. The difference in peak angle may differ by 1°, 0.8°, 0.5°, 0.3°, 0.1°, etc. according to different instruments, different samples, etc. Generally, the tolerance is ±0.2°. Therefore the difference in peak angle cannot be used as the sole criterion. The relative intensity of peaks may vary with samples, sample preparation, and other experimental conditions, so the order of peak intensities cannot be the sole or decisive factor. The influence of experimental factors such as sample height will cause the overall shift of the peak angle, which usually allows a certain shift. Therefore, those skilled in the art can understand that any crystal form having the same or similar characteristic peaks as the X-ray powder diffraction pattern of the present invention belongs to the scope of the present invention. "Single crystalline form" refers to a single crystal form as determined by X-ray powder diffraction.

The co-crystal of the ribociclib or the ribociclib monosuccinate in the present invention is substantially pure, unitary, and substantially free of any other crystal form or amorphous state. "Substantially pure" in the present invention when used in reference to a new crystal form means that this new crystal form comprises at least 80% (by weight) of the present compound, more preferably at least 90% (by weight), and especially at least 95% (by weight), especially at least 99% (by weight).

In the present invention, the starting material, ribociclib, can be obtained by referring to the methods described in Example 74 in patent CN102186856B, or can be purchased commercially. This reference is incorporated into this application by reference in its entirety.

In the present invention, the starting material, ribociclib monosuccinate, can be obtained by referring to the methods described in Example 1 in patent CN105085533A, or can be purchased commercially. This reference is incorporated into this application by reference in its entirety.

The tenth technical problem to be solved by the present invention is to provide a pharmaceutical composition, comprising the co-crystal of ribociclib and saccharin, or the co-crystal of ribociclib and cholic acid, or the co-crystal of ribociclib and orotic acid, or the co-crystal of ribociclib monosuccinate and citric acid, and at least one pharmaceutically acceptable excipient.

Furthermore, the pharmaceutical composition comprises a therapeutically and/or preventively effective amount of one or more the co-crystal of ribociclib and saccharin, or the co-crystal of ribociclib and cholic acid, or the co-crystal of ribociclib and orotic acid, or the co-crystal of ribociclib monosuccinate and citric acid, and at least one pharmaceutically acceptable carrier or auxiliary. In addition, the pharmaceutical composition can further comprise other pharmaceutically acceptable co-crystals of ribociclib or ribociclib monosuccinate. Other pharmaceutically acceptable co-crystal eutectic precursors also include benzoic acid, succinic acid, fumaric acid, malic acid, tartaric acid, adipic acid, benzoic acid, p-aminobenzoic acid, fructose, aspartame, benzyl alcohol, sorbitol, dextrin, maltodextrin, nicotinamide, urea and 2-aminopyrimidine, etc.

Further, the amount of the co-crystals in the pharmaceutical composition is generally in the unit of one percent, and the amount is about 1% to about 99% of the active ingredient, preferably, about 5% to about 7%, most preferably, about 10% to about 30%. In addition, optionally, the pharmaceutical composition may further comprises one or more other pharmaceutically active ingredients, such as ribociclib or ribociclib monosuccinate co-crystal, pharmaceutically acceptable salts, solvates, hydrate crystals or amorphous form thereof.

The pharmaceutical composition can be prepared into solid dosage forms, semi-solid dosage forms or liquid dosage forms. The solid oral dosage forms include, for example, tablets, capsules, granules, pills and powders; the liquid oral dosage forms include, for example, solutions, syrups, suspensions, dispersions and emulsions; the injectable formulations include, for example, solutions, dispersions and lyophilizate. The formulation may be suitable for immediate-release, sustained-release or controlled-release of the active ingredient. The formulation may be a regular, dispersible, chewable, orally soluble or rapidly dissolving form. The administration route of the pharmaceutical composition includes oral administration, intravenous subcutaneous injection, injection into tissue administration, transdermal administration, rectal administration, and intranasal administration, etc. In order to maintain the co-crystal of the present invention during preparation, the pharmaceutical composition in the present invention preferably is the solid oral dosage forms, including tablets, capsules, granules, pills and powders; more preferably, sustained or controlled release solid oral dosage forms.

In the case of solid dosage forms, pharmaceutically acceptable carriers or adjuvants include, but are not limited to: diluents, such as starch, pregelatinized starch, lactose, powdered cellulose, microcrystalline cellulose, calcium hydrogen phosphate, tricalcium phosphate, mannitol, sorbitol, sugar, and the like; binders, such as gum arabic, guar gum, gelatin, polyvinylpyrrolidone, hydroxypropyl cellulose, hydroxypropyl methyl cellulose, polyethylene glycol, and the like; disintegrating agents, such as starch, sodium starch glycolate, pregelatinized starch, crospovidone, croscarmellose sodium, colloidal silica, and the like; lubricants, such as stearic acid, magnesium stearate, zinc stearate, sodium benzoate, sodium acetate, talc, and the like; glidants, such as colloidal silica; complex-forming agents, such as various grades of cyclodextrin and resins; release rate control agents, such as hydroxypropyl cellulose, hydroxymethyl cellulose, hydroxypropyl methyl cellulose, ethyl cellulose, methyl cellulose, methyl methacrylate, wax, and the like. Other pharmaceutically acceptable carriers or adjuvants include, but are not limited to, film formers, plasticizers, colorants, flavoring agents, viscosity modifiers, preservatives, antioxidants, and the like.

The pharmaceutical composition can be prepared by the method commonly known to those skilled in the art. For example, the pharmaceutical composition can be prepared by blending the ribociclib co-crystal or the ribociclib monosuccinate co-crystal in the present invention with one or more pharmaceutically acceptable carrier or auxiliary, optionally with one or more other pharmaceutically active ingredients. The solid dosage form can be prepared by direct blend and granulation process.

The eleventh technical problem to be solved by the present invention is to provide a use of the ribociclib co-crystal or the ribociclib monosuccinate co-crystal in the preparation of medicines for treating cancer.

Furthermore, the present invention provides a use of one or more co-crystals of ribociclib, or the co-crystal of ribociclib monosuccinate in the present invention, or co-crystals of ribociclib or the co-crystal of ribociclib monosuccinate prepared by the present invention in the preparation of medicines for treating cancer.

Further, the present invention provides a method for treating cancer. The method comprises administering to a patient in need thereof a therapeutically effective amount of co-crystals of ribociclib or the co-crystal of ribociclib monosuccinate in the present invention, or pharmaceutical compositions thereof. Patients include, but not limited to mammals.

SPECIFIC IMPLEMENTATIONS

The following examples will help to further understand the present invention, but are not intended to limit the contents of the present invention.

Instruments and characterization methods:

The instrument used for collecting x-ray powder diffraction (XRPD) patterns was Bruker D8 Advance diffractometer. Samples were tested at room temperature under the following test conditions: scan range 3-40° 2θ, step size 0.02° 2θ, and speed 0.2 s/step.

The polarized light microscope (PLM) spectrum was taken from the XP-500E polarized light microscope (Shanghai Chang fang Optical Instrument Co., Ltd.). The objective lens magnification is 4 or 10 times, and the eyepiece magnification is 10 times. The morphology of the sample was observed and photographed.

Thermogravimetric analysis (TGA) data were collected on TA Instruments Q500 TGA. The procedure was as follows: 5~20 mg sample was placed in a platinum pan, using High Resolution TM, and heated at a heating rate of 10° C./min under the protection of dry nitrogen purge at 40 mL/min.

Differential thermal analysis (DSC) data were collected on TA Instruments Q200 MDSC. The procedure was as follows: 1~10 mg sample was placed in a sealed aluminum pan, and heated at a heating rate of 10° C./min under the protection of dry nitrogen purge at 40 mL/min.

Single crystal diffractometer: Eos CCD detector, four-round Kappa meter, enhanced Mo light source and enhanced Cu light source. Detection parameters: ambient temperature 106K, enhanced Cu light source, graphite monochromator, wavelength 1.54 Å.

1H Nuclear magnetic resonance spectrum (1H-NMR) data were collected on Bruker Ascen II DMX 500 MHZ nuclear magnetic resonance spectrometer. 1~5 mg sample was weighed, dissolved with approximately 0.5 mL of deuterated reagent in a NMR sample tube for testing.

Unless particularly specified, all examples were performed at room temperature, the solvent ratios were all volume ratios.

Unless particularly specified, all reagents used in the examples were commercially available.

The ultrasonic operation in examples can promote the dissolution of the sample.

The equipment is an ultrasonic cleaner, which is performed at a power of 40 kHz for 15 minutes.

Preparation Example 1

Ribociclib was obtained by referring to the preparation method of Example 74 in patent document CN102186856B.

Figure 1:
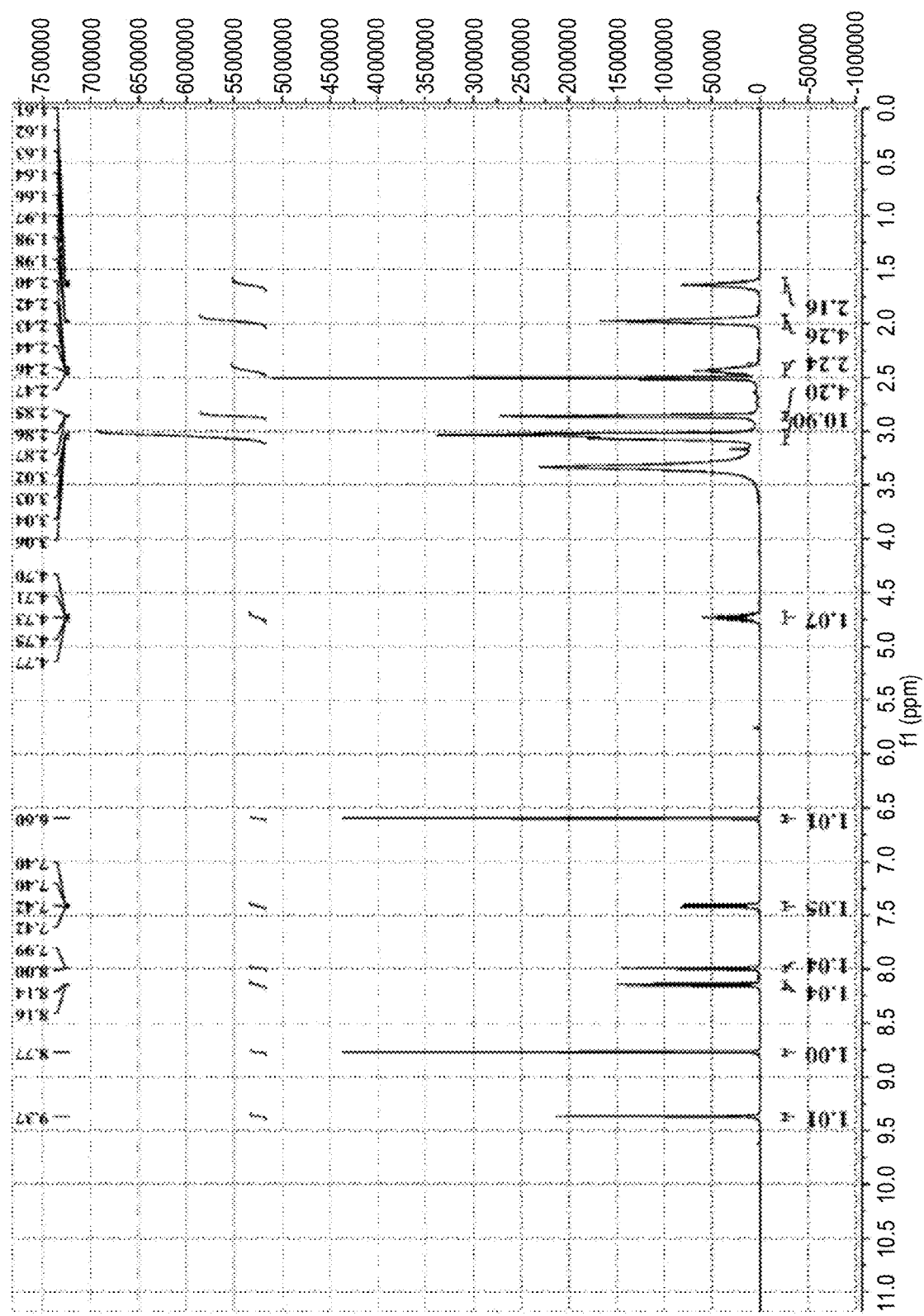
FIG. 1 is the $^1$HNMR spectrum of ribociclib prepared with reference to CN101575333B.

The ¹HNMR spectrum, shown in FIG. 1, Shows that the obtained sample is same as Ribociclib prepared by the method of Example 74 in patent document CN102186856B.

Preparation Example 2

The crystal Form I of ribociclib monosuccinate was obtained by referring to the preparation method of Example 1 in patent document CN105085533A.

Figure 2:
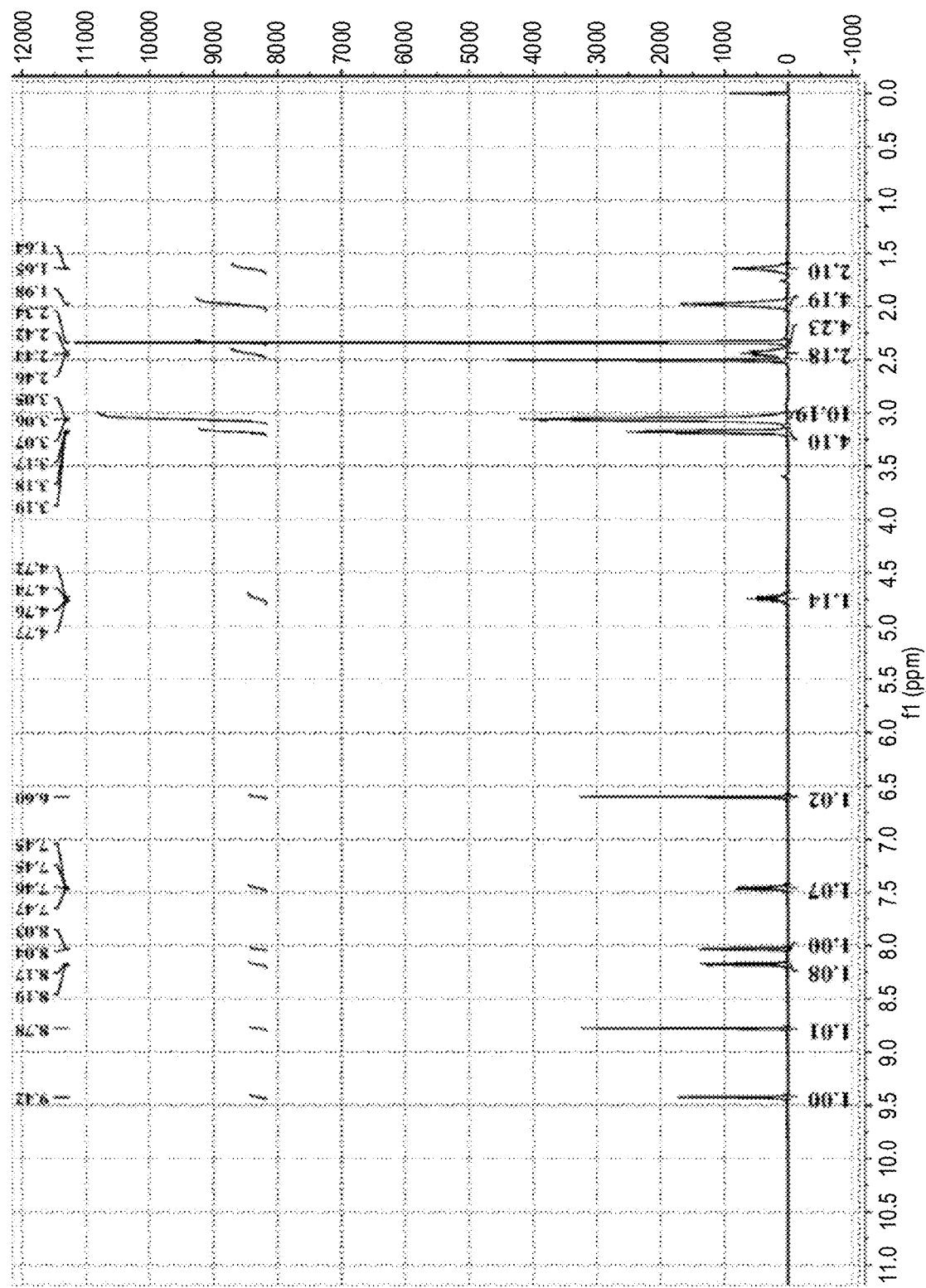
FIG. 2 is the X-ray powder diffraction pattern of the co-crystal of ribociclib and MEK prepared with reference to Example 1 in CN105461702A.

The ¹HNMR spectrum, shown in FIG. 2, Shows that the obtained sample is same as Ribociclib monosuccinate prepared by the method of Example 1 in patent document CN105085533A. HPLC: a maximum single impurity of 1.43% at the RRT of 1.403.

Preparation Example 3

The co-crystal Form III of ribociclib and MEK162 was obtained by referring to the preparation method of Example 5 in patent document CN105753869A.

Figure 3:
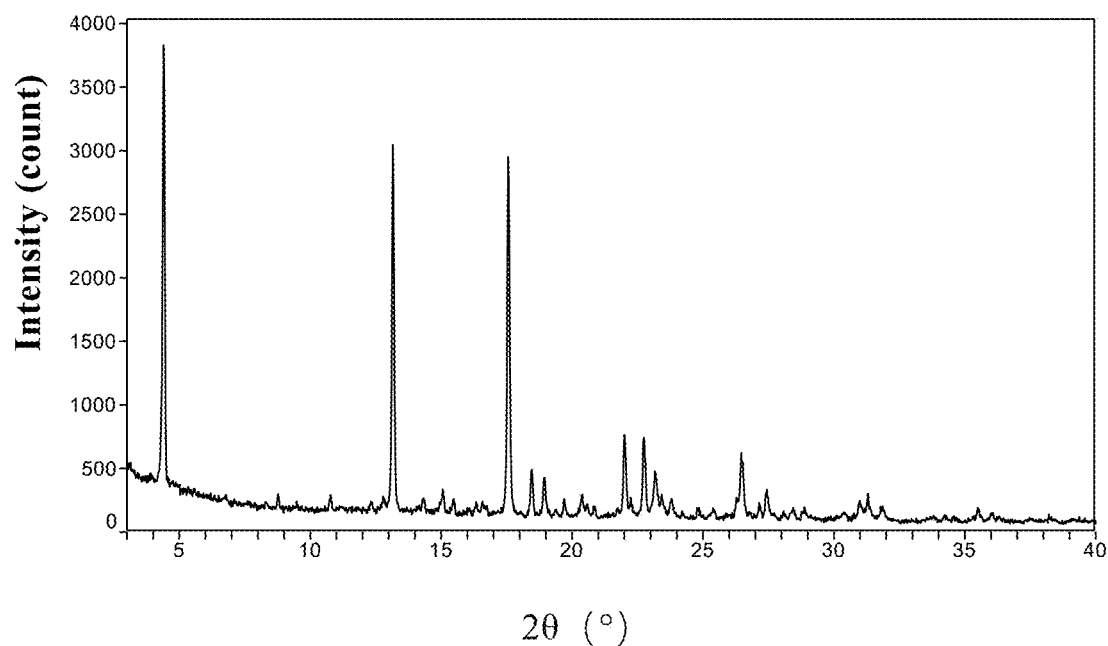
FIG. 3 is the X-ray powder diffraction pattern of the co-crystal of ribociclib and MEK prepared with reference to Example 1 in CN105461702A.

The XRPD pattern, shown in FIG. 3, Shows that the crystal form of the obtained sample is same as the co-crystal Form III of ribociclib and MEK162 describe in Example 5 of patent document CN105753869A.

Example 1

Took ribociclib (10 mg) from Preparation Example 1 and saccharin (4.2 mg, 1 equivalent), added 2 mL methanol, sonicated for dissolution and volatilized at room temperature to obtain the co-crystal of ribociclib and saccharin in the present invention.

Example 2

Took ribociclib (10 mg) from Preparation Example 1 and saccharin (4.2 mg, 1 equivalent), added 10.0 mL ethanol, sonicated for dissolution and volatilized at room temperature to obtain the co-crystal of ribociclib and saccharin in the present invention.

Example 3

Took ribociclib (10 mg) from Preparation Example 1 and saccharin (4.2 mg, 1 equivalent), added a mixed solvent of acetonitrile and water (1.0 mL, 1:1) sonicated for dissolution and volatilized at 35° C. to obtain the co-crystal of ribociclib and saccharin in the present invention.

Example 4

Took ribociclib (25 mg) from Preparation Example 1 and saccharin (10.5 mg, 1 equivalent), added a mixed solvent of ethyl acetate and acetone (1.0 mL, 2:1) sonicated for dissolution and volatilized at 40° C. to obtain the co-crystal of ribociclib and saccharin in the present invention.

Example 5

Took ribociclib (50 mg) from Preparation Example 1, added methanol (1 mL) and saccharin (21.0 mg, 1 equivalent), stirred at room temperature for 30 hours, then filtered under reduced pressure. The filter cake was dried at 40° C. under vacuum for 10 hours to obtain the co-crystal of ribociclib and saccharin in the present invention (68.2 mg).

Example 6

Took ribociclib (50 mg) from Preparation Example 1, added a mixed solvent of ethanol and tetrahydrofuran (1.5 mL, 1:1) and saccharin (31.6 mg, 1.5 equivalents), stirred at room temperature for 24 hours, then filtered under reduced pressure. The filter cake was dried at 25° C. under vacuum for 24 hours to obtain the co-crystal of ribociclib and saccharin in the present invention (67.3 mg).

Example 7

Took ribociclib (50 mg) from Preparation Example 1, added a mixed solvent of methanol and water (1.0 mL, 1:1) and saccharin (42.2 mg, 2 equivalents), stirred at room temperature for 72 hours, then filtered under reduced pressure. The filter cake was dried at 30° C. under vacuum for 20 hours to obtain the co-crystal of ribociclib and saccharin in the present invention (65.1 mg).

Example 8

Took ribociclib (50 mg) from Preparation Example 1, added a mixed solvent of isopropanol and water (2.0 mL, 1:1) and saccharin (21 mg, 1 equivalent), stirred at 40° C. for 8 hours, then filtered under reduced pressure. The filter cake was dried at 40° C. under vacuum for 36 hours to obtain the co-crystal of ribociclib and saccharin in the present invention (56.1 mg).

Example 9

Took ribociclib (50 mg) from Preparation Example 1 and saccharin (10.5 mg, 0.5 equivalent), added acetone (0.5 mL). After the mixture was completely wetted with acetone at room temperature, ground to dryness to obtain the co-crystal of ribociclib and saccharin in the present invention.

Example 10

Took ribociclib (30 mg) from Preparation Example 1 and saccharin (12.6 mg, 1 equivalent), added a mixed solvent of methanol and water (0.5 mL, 1:1). After the mixture was completely wetted with the mixed solvent of methanol and water (1:1) at room temperature, ground to dryness to obtain the co-crystal of ribociclib and saccharin in the present invention.

Example 11

Took ribociclib (30 mg) from Preparation Example 1 and saccharin (25.2 mg, 2 equivalents), added dichloromethane (0.6 mL). After the mixture was completely wetted with dichloromethane at 40° C., ground to dryness to obtain the co-crystal of ribociclib and saccharin in the present invention.

Example 12

Took ribociclib (30 mg) from Preparation Example 1 and saccharin (12.6 mg, 1 equivalent), added tetrahydrofuran (0.4 mL). After the mixture was completely wetted with tetrahydrofuran at 40° C., then ground to dryness to obtain the co-crystal of ribociclib and saccharin in the present invention.

Example 13

Took ribociclib (15 mg) from Preparation Example 1 and saccharin (6.3 mg, 1 equivalent), added a mixed solvent of 1,4-dioxane and water (1.5 mL, 1:1), heated to 55° C. and stirred for dissolution, cooled to 4° C. at a cooling rate of 5° C./hour, stirred for 3 days, then filtered under reduced pressure. The filter cake was dried at 25° C. under vacuum for 24 hours to obtain the co-crystal of ribociclib and saccharin in the present invention (14 mg).

Example 14

Took ribociclib (15 mg) from Preparation Example 1 and saccharin (9.5 mg, 1.5 equivalents), added a mixed solvent of acetone and water (0.5 mL, 1:2), heated to 60° C. and stirred for dissolution, cooled to 6° C. at a cooling rate of 8° C./hour, stirred for 5 days, then filtered under reduced pressure. The filter cake was dried at 25° C. under vacuum for 48 hours to obtain the co-crystal of ribociclib and saccharin in the present invention (13 mg).

Example 15

Took ribociclib (15 mg) from Preparation Example 1 and saccharin (12.6 mg, 2 equivalents), added a mixed solvent of methanol and butanone (1.5 mL, 4:1), heated to 50° C. and stirred for dissolution, cooled to room temperature at a cooling rate of 10° C./hour, stirred for 1 day, then filtered under reduced pressure. The filter cake was dried at 40° C. under vacuum for 10 hours to obtain the co-crystal of ribociclib and saccharin in the present invention (13 mg).

Example 16

Took ribociclib (50 mg) from Preparation Example 1 and saccharin (21 mg, 1 equivalent), added a mixed solvent of ethanol and dimethyl sulfoxide (1 mL, 4:1), heated to 60° C. and stirred for dissolution, cooled to room temperature at a cooling rate of 6° C./hour, stirred for 1 day, then filtered under reduced pressure. The filter cake was dried at 40° C. under vacuum for 24 hours to obtain the co-crystal of ribociclib and saccharin in the present invention (48 mg).

Example 17

The co-crystal of ribociclib and saccharin can be obtained by replacing the solvents in Example 2, Example 6, Example 9, and Example 15 with the following solvents in the table below.

| Experiment Number | Solvents |
| --- | --- |
| Experiment 1 | trifluoroethanol/isobutyl acetate |
| Experiment 2 | n-butanol |
| Experiment 3 | ethanol/methyl tert-butyl ether |
| Experiment 4 | methanol/ether |
| Experiment 5 | tetrahydrofuran/n-heptane |
| Experiment 6 | acetone/cyclohexane |

Example 18

Figure 4:
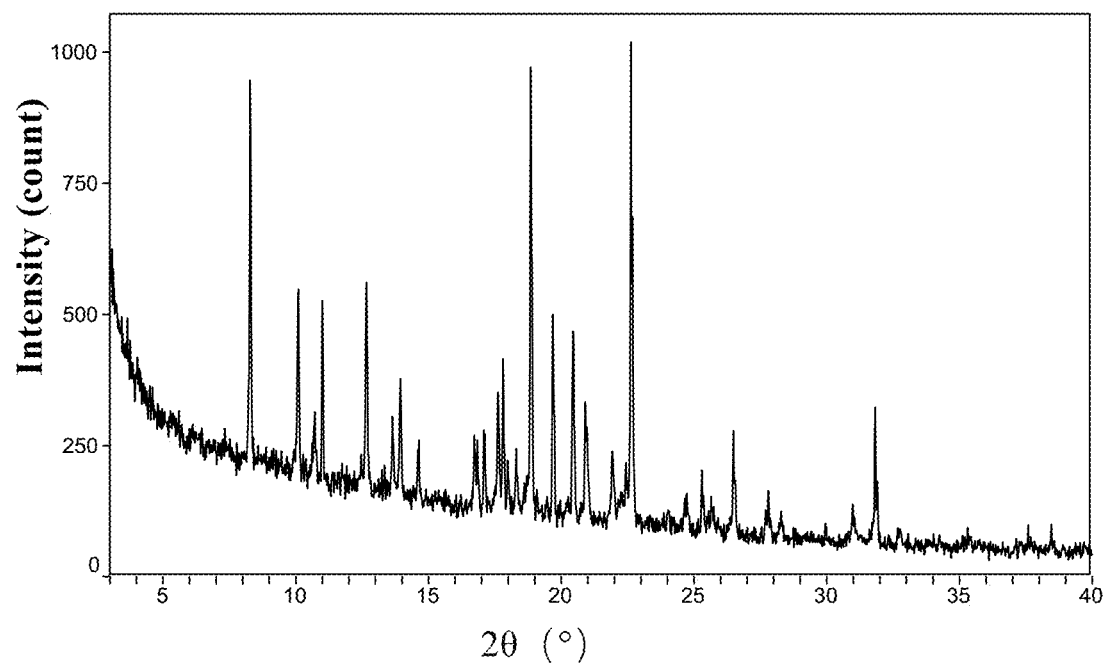
FIG. 4 is the X-ray powder diffraction pattern of the co-crystal of ribociclib and saccharin in the present invention.

The co-crystal of ribociclib and saccharin obtained from Example 2 was subjected to XRPD characterization. The X-ray powder diffraction pattern is shown in FIG. 4.

Figure 5:
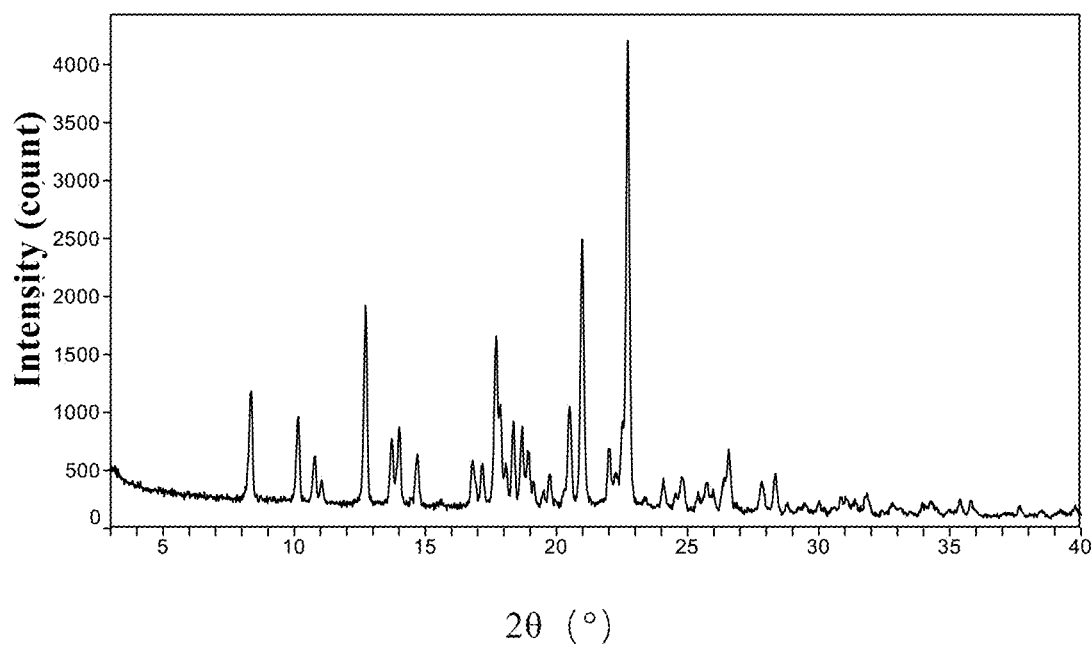
FIG. 5 is the X-ray powder diffraction pattern of the co-crystal of ribociclib and saccharin in the present invention.
Figure 7:
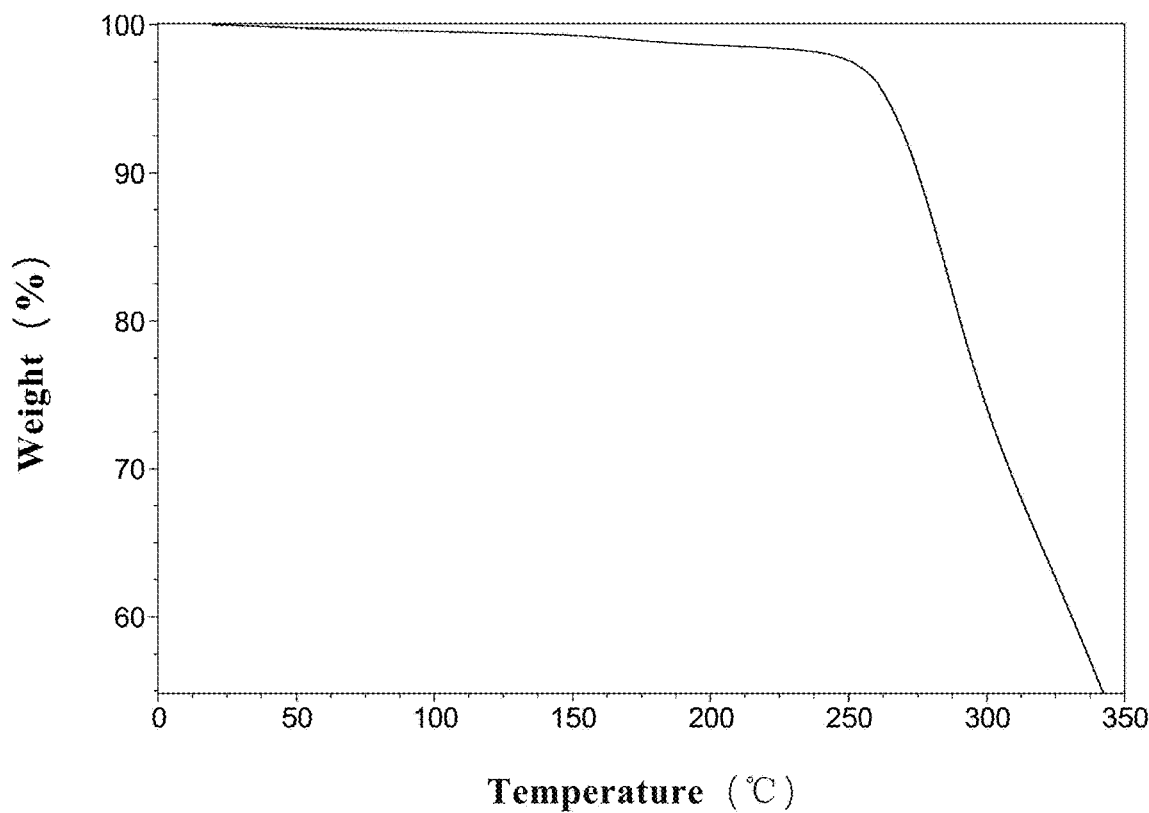
FIG. 7 is the TGA thermogram of the co-crystal of ribociclib and saccharin in the present invention.
Figure 8:
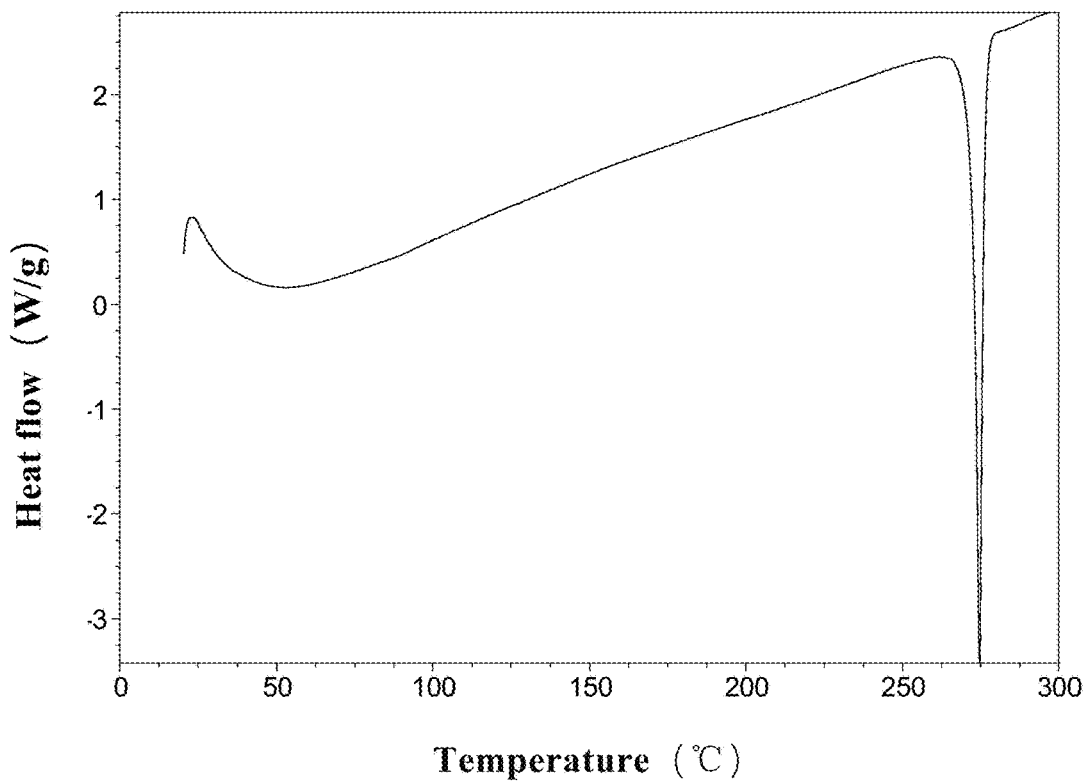
FIG. 8 is the DSC thermogram of the co-crystal of ribociclib and saccharin in the present invention.
Figure 9:
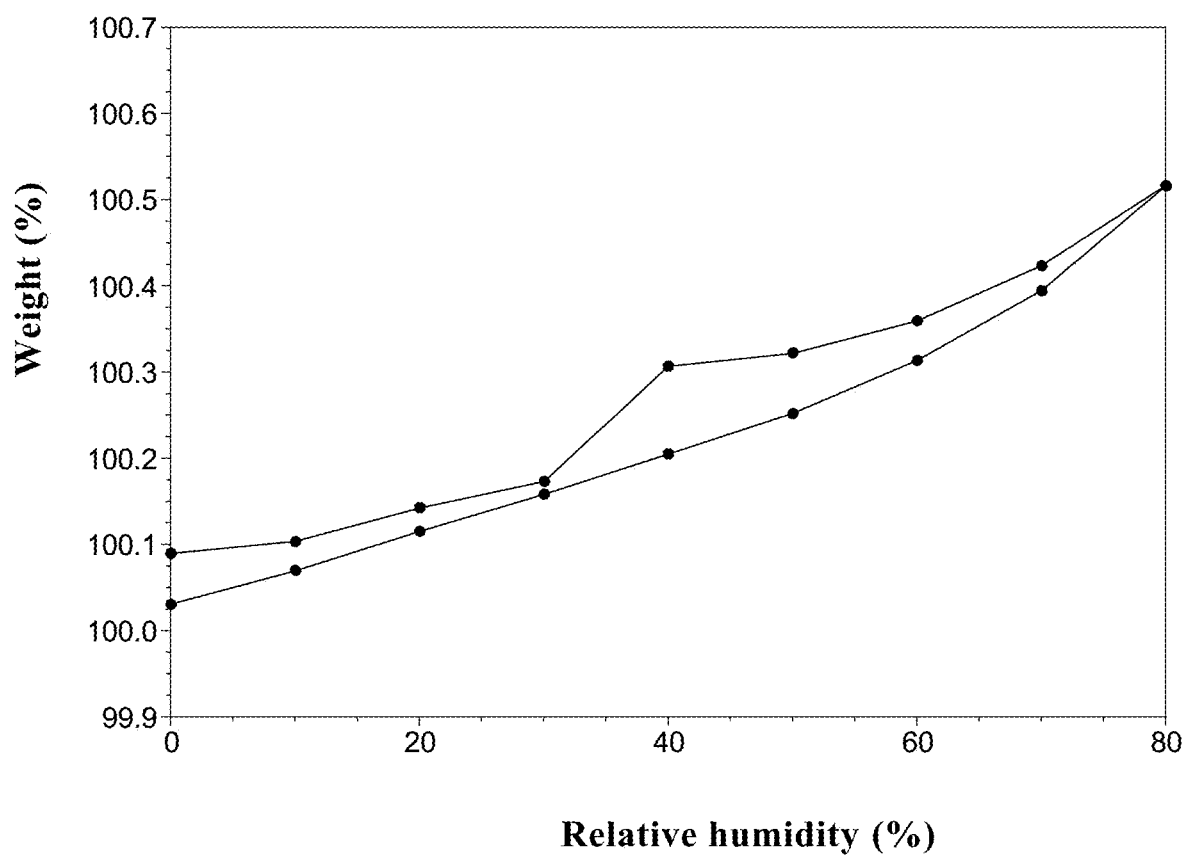
FIG. 9 is the isothermal sorption curve of the co-crystal of ribociclib and saccharin in the present invention.
Figure 10:
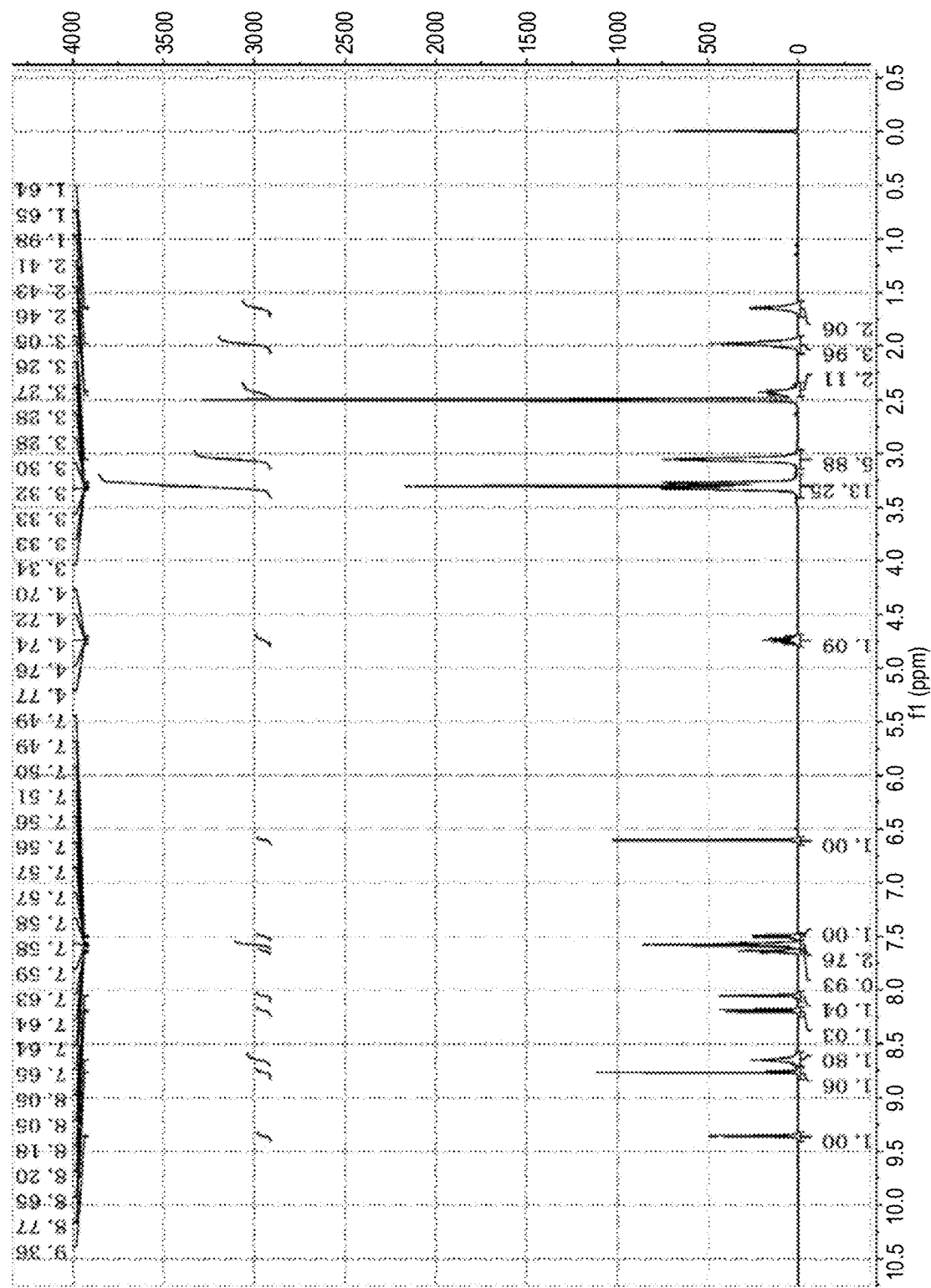
FIG. 10 is the $^1$HNMR spectrum of the co-crystal of ribociclib and saccharin in the present invention.

The co-crystal of ribociclib and saccharin obtained from Example 6 was subjected to characterization. The X-ray powder diffraction pattern is shown in FIG. 5. The TGA thermogram is shown in FIG. 7, showing that it is an anhydrate. The DSC thermogram is shown in FIG. 8, showing that the melting point is 272° C. The isothermal adsorption curve is shown in FIG. 9, showing that there is a weight gain of 0.04% at a relative humidity of 0-10%, and a weight gain of 0.45% at a relative humidity of 10 to 80%. The $^1$HNMR spectrum is shown in FIG. 10, showing that the molar ratio of ribociclib to saccharin is 1:1.

Figure 6:
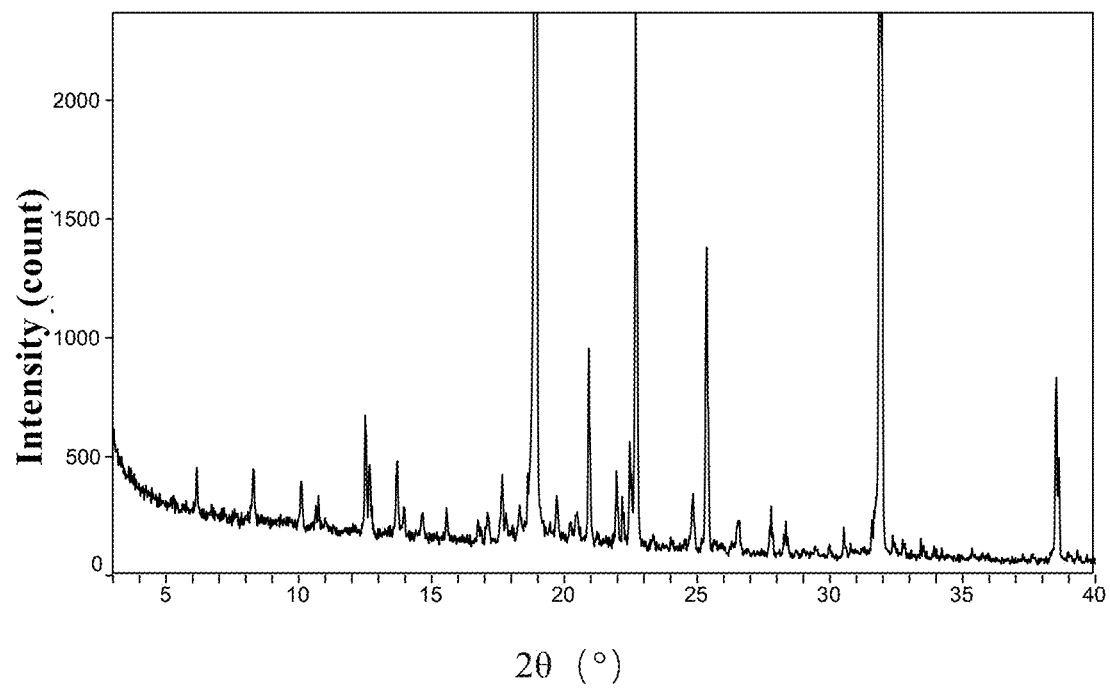
FIG. 6 is the X-ray powder diffraction pattern of the co-crystal of ribociclib and saccharin in the present invention.

The co-crystal of ribociclib and saccharin obtained from Example 15 was subjected to XRPD characterization. The X-ray powder diffraction pattern is shown in FIG. 6.

The samples prepared in Example 1 to 17 had the same or similar XRPD pattern (not shown), DSC thermogram (not shown), TGA thermogram (not shown) and HNMR spectrum (not shown) as the sample in Example 2, 6 and 15. It indicates that the sample in Examples 1 to 17 are the same co-crystal compound.

Example 19

A mixed solvent of methanol and water (1.0 mL, 1:1) and cholic acid (47.0 mg) were added to ribociclib (50 mg) from Preparation Example 1, stirred at room temperature for 24 hours, then filtered under reduced pressure. The filter cake was dried at 40° C. under vacuum for 16 hours to obtain the co-crystal Form I of ribociclib and cholic acid in the present invention (92.7 mg).

Example 20

Ethanol (5 mL) and cholic acid (70.5 mg) were added to ribociclib (50 mg) from Preparation Example 1, stirred at room temperature for 36 hours, then filtered under reduced pressure. The filter cade was dried at 25° C. under vacuum for 24 hours to obtain the co-crystal Form I of ribociclib and cholic acid in the present invention (91.2 mg).

Example 21

A mixed solvent of acetonitrile and water (1.5 mL, 4:1) and cholic acid (94.0 mg) were added to ribociclib (50 mg) from Preparation Example 1, stirred at room temperature for 72 hours, then filtered under reduced pressure. The filter cake was dried at 30° C. under vacuum for 24 hours to obtain the co-crystal Form I of ribociclib and cholic acid in the present invention (89.3 mg).

Example 22

A mixed solvent of isopropanol and tetrahydrofuran (2.0 ml, 1:1) was added to ribociclib (50 mg) from Preparation Example 1. A solution of cholic acid (141.0 mg) in a mixed solvent of isopropanol and tetrahydrofuran (5.0 mL, 1:1) was added to the suspension of ribociclib under stirring, stirred at 40° C. for 48 hours, then filtered under reduced pressure. The filter cake was dried at 40° C. under vacuum for 48 hours to obtain the co-crystal Form I of ribociclib and cholic acid in the present invention (83.6 mg).

Example 23

The co-crystal Form I of ribociclib and cholic acid can be obtained by replacing the solvents in Example 22 with the following solvents in the table below.

| Experiment Number | Solvent |
| --- | --- |
| Experiment 1 | methanol |
| Experiment 2 | acetone |
| Experiment 3 | water |
| Experiment 4 | a mixed solvent of trifluoroethanol and water |
| Experiment 5 | a mixed solvent of n-propanol and water |
| Experiment 6 | a mixed solvent of methyl tert-butyl ether and methanol |
| Experiment 7 | a mixed solvent of methyl ethyl ketone and ethanol |
| Experiment 8 | a mixed solvent of n-heptane and acetone |
| Experiment 9 | a mixed solvent of acetone and isopropyl acetate |

Example 24

Took ribociclib (30 mg) from Preparation Example 1 and cholic acid (28.2 mg), added methanol (0.6 mL). After the mixture was completely wetted with methanol at room temperature, then ground to dryness to obtain the co-crystal Form I of ribociclib and cholic acid in the present invention.

Example 25

Took ribociclib (30 mg) from Preparation Example 1 and cholic acid (28.2 mg), added tetrahydrofuran (0.6 mL). After the mixture was completely wetted with tetrahydrofuran at 35° C., then ground to dryness to obtain the co-crystal Form I of ribociclib and cholic acid in the present invention.

Example 26

Took ribociclib (30 mg) from Preparation Example 1 and cholic acid (28.2 mg), added acetone (1.5 mL). After the mixture was completely wetted with acetone at 40° C., then ground to dryness to obtain the co-crystal Form I of ribociclib and cholic acid in the present invention.

Example 27

The co-crystal Form I of ribociclib and cholic acid can be obtained by replacing the solvents in Example 26 with the following solvents in the table below.

| Experiment Number | Solvent |
| --- | --- |
| Experiment 1 | ethanol |
| Experiment 2 | dichloromethane |
| Experiment 3 | water |
| Experiment 4 | a mixed solvent of ethyl acetate and dimethyl sulfoxide |
| Experiment 5 | a mixed solvent of isopropyl ether and methanol |
| Experiment 6 | n-heptane |

Example 28

Took ribociclib (10 mg) from Preparation Example 1 and cholic acid (9.4 mg), added methanol (2.0 mL), sonicated for dissolution and volatilized at room temperature to obtain the co-crystal Form I of ribociclib and cholic acid in the present invention.

Example 29

Took ribociclib (10 mg) from Preparation Example 1 and cholic acid (9.4 mg), added ethanol (5 mL), sonicated for dissolution and volatilized at room temperature to obtain the co-crystal Form I of ribociclib and cholic acid in the present invention.

Example 30

Took ribociclib (10 mg) from Preparation Example 1 and cholic acid (9.4 mg), added a mixed solvent of methanol and water (1.0 mL, 1:1), sonicated for dissolution and volatilized at 35° C. to obtain the co-crystal Form I of ribociclib and cholic acid in the present invention.

Example 31

Took ribociclib (10 mg) from Preparation Example 1 and cholic acid (9.4 mg), added a mixed solvent of isopropyl acetate and trifluoroethanol (3.0 mL, 2:1), sonicated for dissolution and volatilized at 40° C. to obtain the co-crystal Form I of ribociclib and cholic acid in the present invention.

Example 32

The co-crystal Form I of ribociclib and cholic acid can be obtained by replacing the solvents in Example 31 with the following solvents in the table below.

| Experiment Number | Solvent |
| --- | --- |
| Experiment 1 | isopropanol |
| Experiment 2 | dimethyl sulfoxide |
| Experiment 3 | a mixed solvent of ethyl acetate and methanol |
| Experiment 4 | a mixed solvent of ethanol and chloroform |
| Experiment 5 | a mixed solvent of acetone and methylcyclohexane |
| Experiment 6 | a mixed solvent of methanol and isopropyl ether |

Example 33

Took ribociclib (15 mg) from Preparation Example 1 and cholic acid (14.1 mg), added methanol (1.0 mL), heated to 60° C. and stirred for dissolution, cooled to 4° C. at a cooling rate of 6° C./hour, stirred for 3 days, then filtered under reduced pressure. The filter cake was dried at 25° C. under vacuum for 24 hours to obtain the co-crystal Form I of ribociclib and cholic acid in the present invention (27.3 mg).

Example 34

Took ribociclib (15 mg) from Preparation Example 1 and cholic acid (21.2 mg), added a mixed solvent of ethanol and water (0.6 ml, 1:2), heated to 60° C. and stirred for dissolution, cooled to 4° C. at a cooling rate of 8° C./hour, stirred for 5 days, then filtered under reduced pressure. The filter cake was dried at 30° C. under vacuum for 48 hours to obtain the co-crystal Form I of ribociclib and cholic acid in the present invention (26.5 mg).

Example 35

Took ribociclib (15 mg) from Preparation Example 1 and cholic acid (28.2 mg), added a mixed solvent of 1,4-dioxane and water (0.8 ml, 2:1), heated to 50° C. and stirred for dissolution, cooled to room temperature at a cooling rate of 10° C./hour, stirred for 1 day, then filtered under reduced pressure. The filter cake was dried at 40° C. under vacuum for 10 hours to obtain the co-crystal Form I of ribociclib and cholic acid in the present invention (25.9 mg).

Example 36

Took ribociclib (15 mg) from Preparation Example 1 and cholic acid (9.4 mg), added a mixed solvent of acetone and dimethyl sulfoxide (0.5 ml, 3:1), heated to 55° C. and stirred for dissolution, cooled to room temperature at a cooling rate of 5° C./hour, stirred for 1 day, then filtered under reduced pressure. The filter cake was dried at 40° C. under vacuum for 24 hours to obtain the co-crystal Form I of ribociclib and cholic acid in the present invention (16.2 mg).

Example 37

The co-crystal Form I of ribociclib and cholic acid can be obtained by replacing the solvents in Example 36 with the following solvents in the table below.

| Experiment Number | Solvent |
| --- | --- |
| Experiment 1 | ethanol |
| Experiment 2 | a mixed solvent of ethanol and n-heptane |
| Experiment 3 | a mixed solvent of isopropyl acetate and methanol |
| Experiment 4 | a mixed solvent of acetone and n-heptane |
| Experiment 5 | a mixed solvent of methyl ethyl ketone and isopropyl ether |

Example 38

Figure 11:
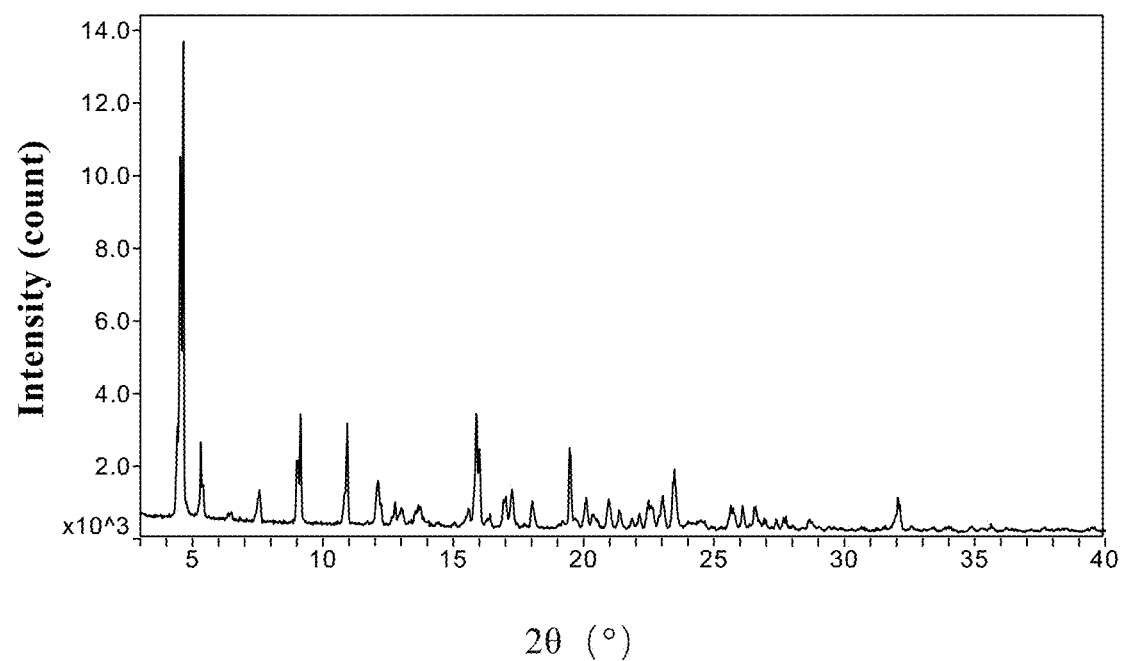
FIG. 11 is the X-ray powder diffraction pattern of the co-crystal Form I of ribociclib and cholic acid in the present invention.
Figure 12:
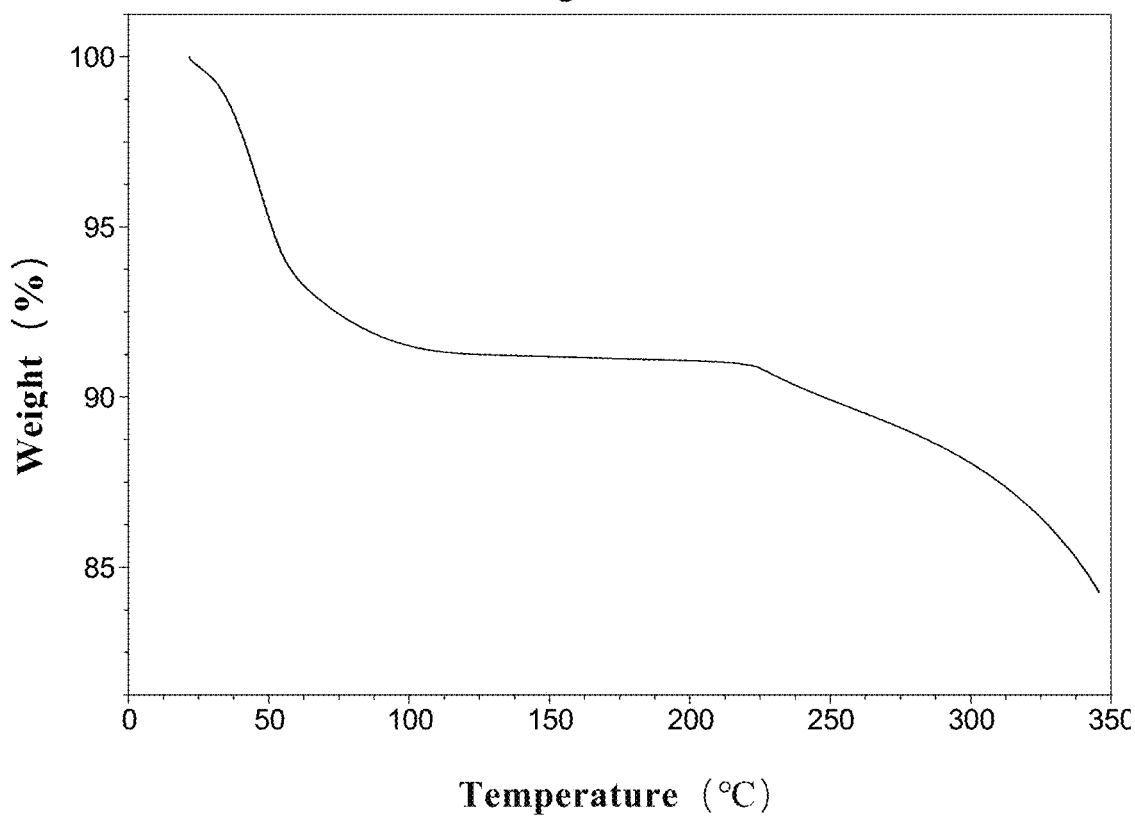
FIG. 12 is the TGA thermogram of the co-crystal Form I of ribociclib and cholic acid in the present invention.
Figure 13:
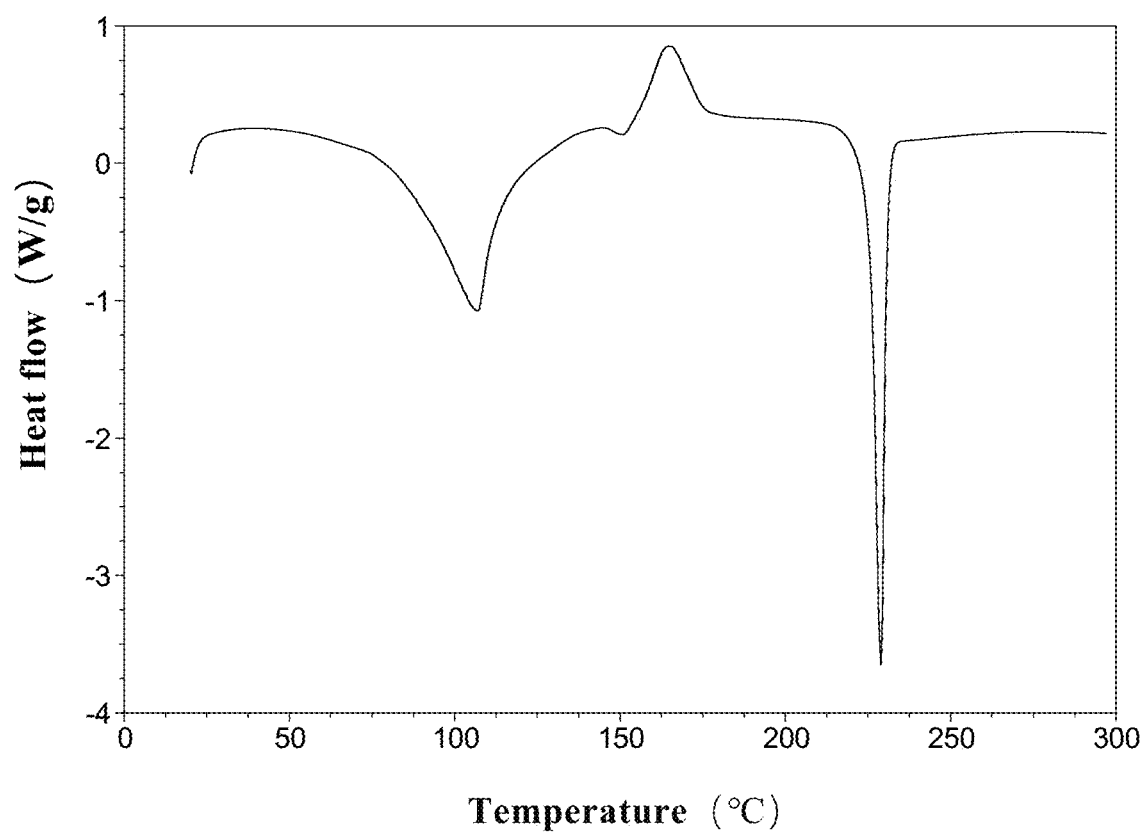
FIG. 13 is the DSC thermogram of the co-crystal Form I of ribociclib and cholic acid in the present invention.
Figure 14:
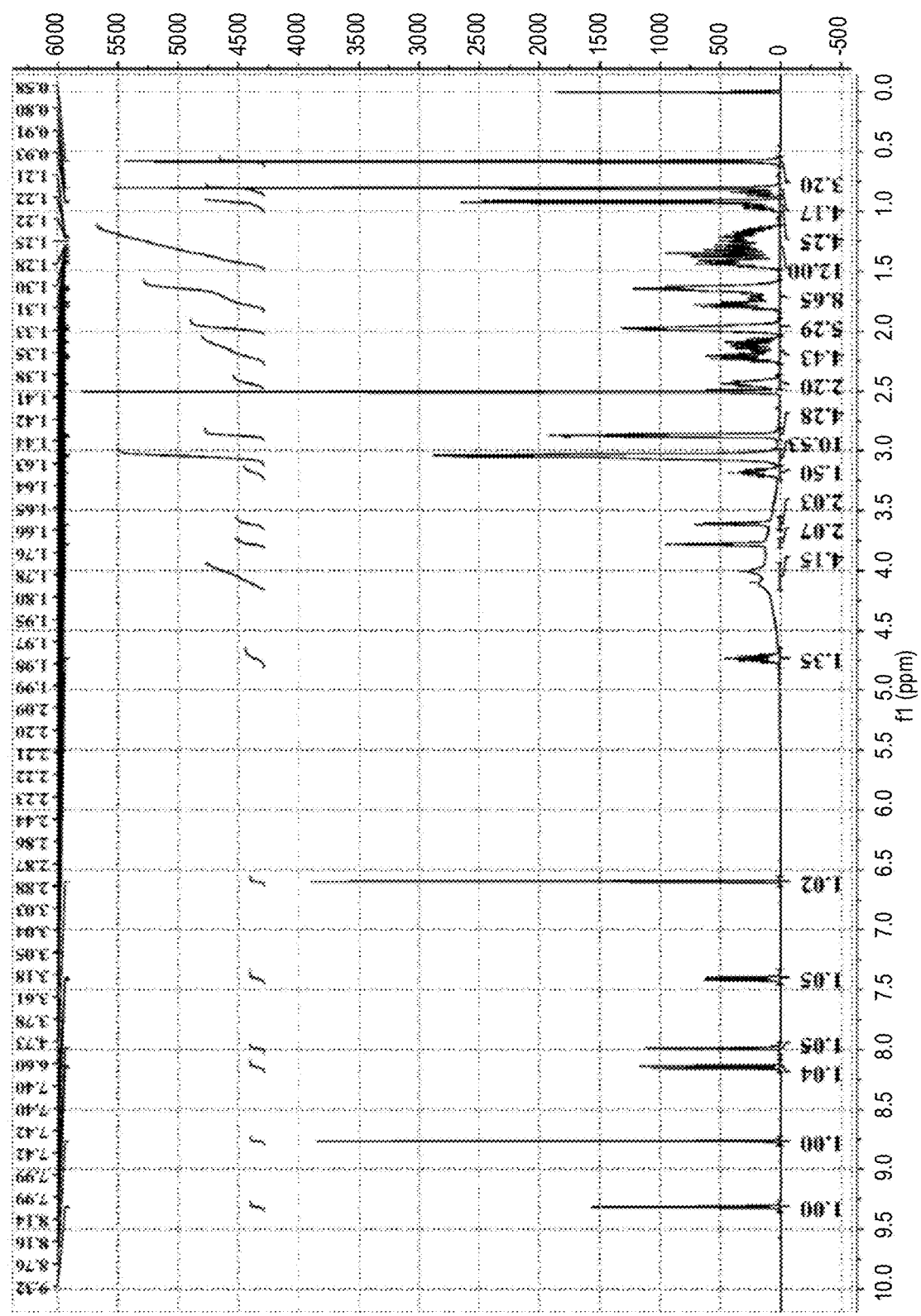
FIG. 14 is the $^1$HNMR spectrum of the co-crystal Form I of ribociclib and cholic acid in the present invention.

The co-crystal Form I of ribociclib and cholic acid obtained from Example 19 was subjected to characterization. The X-ray powder diffraction pattern is shown in FIG. 11. The TGA thermogram is shown in FIG. 12, showing that it is an anhydrate. The DSC thermogram is shown in FIG. 13, showing that the melting point is 226° C. The $^1$HNMR spectrum is shown in FIG. 14, showing that the molar ratio of ribociclib to cholic acid is 1:1.

The samples prepared in Examples 20 to 37 had the same or similar XRPD pattern, DSC thermogram, TGA thermogram and HNMR spectrum (not shown) as the sample in Example 19. It indicates that the samples in Examples 20 to 37 and the sample in Example 19 have the same co-crystal form

Example 39

The co-crystal Form I of ribociclib and cholic acid from Example 19 (20 mg) was heated to 60° C. at a rate of 5° C./min, then remained at 60° C. for 5 minutes to obtain the co-crystal Form II of ribociclib and cholic acid.

Figure 15:
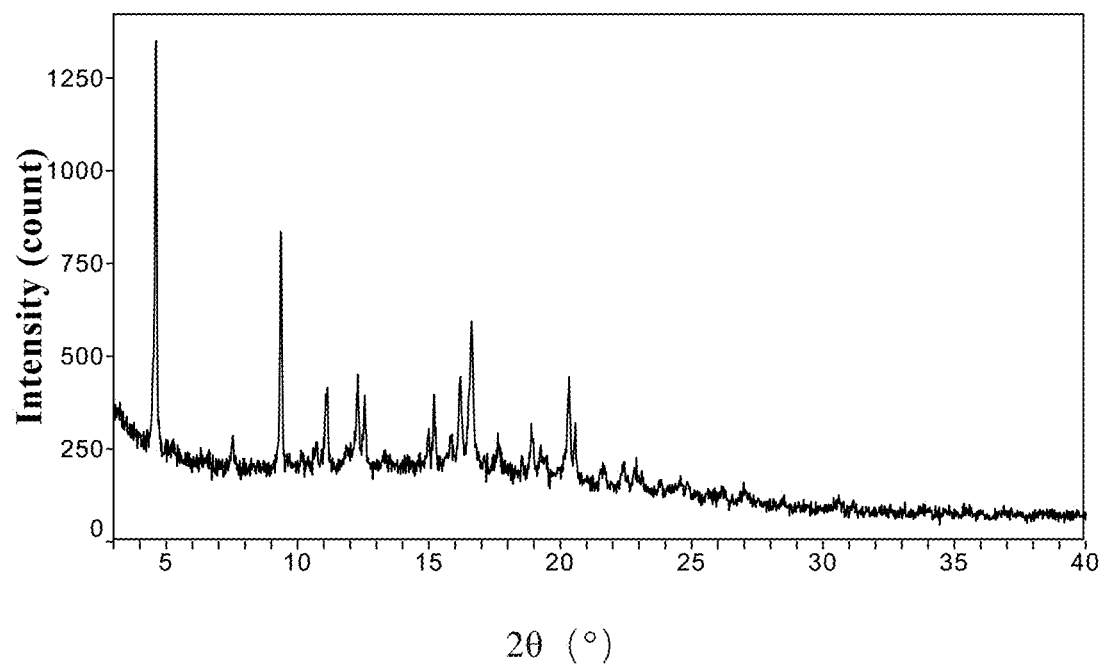
FIG. 15 is the X-ray powder diffraction pattern of the co-crystal Form II of ribociclib and cholic acid in the present invention.

The X-ray powder diffraction pattern is shown in FIG. 15.

Example 40

The co-crystal Form I of ribociclib and cholic acid from Example 19 (20 mg) was heated to 80° C. at a rate of 10° C./min, then remained at 80° C. for 30 minutes to obtain the co-crystal Form II of ribociclib and cholic acid.

Example 41

The co-crystal Form I of ribociclib and cholic acid from Example 20 (25 mg) was heated to 100° C. at a rate of 10° C./min, then remained at 100° C. for 10 minutes to obtain the co-crystal Form II of ribociclib and cholic acid.

The samples prepared in Examples 40 to 41 had the same or similar XRPD pattern as the sample in Example 39. It indicates that the sample in Examples 40 to 41 and the sample in Example 39 have the same co-crystal form

Example 42

A mixed solvent of ethanol and water (1.8 mL, 1:1) and orotic acid (18.0 mg) were added to ribociclib (50 mg) from Preparation Example 1, stirred at room temperature for 36 hours, then filtered under reduced pressure. The filter cake was dried at 40° C. under vacuum for 24 hours to obtain the co-crystal Form I of ribociclib and orotic acid in the present invention (64.6 mg).

Example 43

A mixed solvent of acetone and water (2.6 mL, 1:2) and orotic acid (26.9 mg) were added to ribociclib (50 mg) from Preparation Example 1, stirred at room temperature for 72 hours, then filtered under reduced pressure. The filter cake was dried at 25° C. under vacuum for 10 hours to obtain the co-crystal Form I of ribociclib and orotic acid in the present invention (62.8 mg).

Example 44

A mixed solvent of methanol and water (1.5 mL, 2:1) and orotic acid (35.9 mg) were added to ribociclib (50 mg) from Preparation Example 1, stirred at room temperature for 24 hours, then filtered under reduced pressure. The filter cake was dried at 30° C. under vacuum for 24 hours to obtain the co-crystal Form I of ribociclib and orotic acid in the present invention (60.3 mg).

Example 45

Took ribociclib (50 mg) from Preparation Example 1, added a mixed solvent of tetrahydrofuran and water (1.8 ml, 1:2), added a solution of orotic acid (53.9 mg) in a mixed solvent of tetrahydrofuran and water (2.0 mL, 1:2) to the suspension of ribociclib under stirring, stirred at 40° C. for 48 hours, then filtered under reduced pressure. The filter cake was dried at 40° C. under vacuum for 48 hours to obtain the co-crystal Form I of ribociclib and orotic acid in the present invention (52.3 mg).

Example 46

The co-crystal Form I of ribociclib and orotic acid can be obtained by replacing the solvents in Example 45 with the following solvents in the table below.

| Experiment Number | Solvent |
| --- | --- |
| experiment 1 | methanol |
| experiment 2 | acetone |
| experiment 3 | a mixed solvent of acetonitrile and water |
| experiment 4 | a mixed solvent of isopropanol and water |
| experiment 5 | a mixed solvent of isopropyl ether and methanol |
| experiment 6 | a mixed solvent of methyl ethyl ketone and n-butyl alcohol |
| experiment 7 | The mixed solvent of n-heptane and acetone |
| experiment 8 | a mixed solvent of dichloromethane and isopropyl acetate |

Example 47

Ethanol (0.6 mL) was added to ribociclib (30 mg) from Preparation Example 1 and orotic acid (10.8 mg). After the mixture was completely wetted with ethanol at room temperature, then ground to dryness to obtain the co-crystal Form I of ribociclib and orotic acid in the present invention.

Example 48

Water (0.5 mL) was added to ribociclib (30 mg) from Preparation Example 1 and orotic acid (10.8 mg). After the mixture was completely wetted with water at room temperature, then ground to dryness to obtain the co-crystal Form I of ribociclib and orotic acid in the present invention.

Example 49

Dichloromethane (1.5 mL) was added to ribociclib (30 mg) from Preparation Example 1 and orotic acid (10.8 mg). After the mixture was completely wetted with dichloromethane at room temperature, then ground to dryness to obtain the co-crystal Form I of ribociclib and orotic acid in the present invention.

Example 50

The co-crystal Form I of ribociclib and orotic acid can be obtained by replacing the solvent in Example 49 with the following solvents in the table below.

| Experiment Number | Solvent |
| --- | --- |
| Experiment 1 | methanol |
| Experiment 2 | tetrahydrofuran |
| Experiment 3 | a mixed solvent of acetonitrile and n-butanol |
| Experiment 4 | a mixed solvent of ethyl acetate and dimethyl sulfoxide |
| Experiment 5 | a mixed solvent of methyl tert-butyl ether and methanol |
| Experiment 6 | a mixed solvent of n-heptane and acetone |

Example 51

Took ribociclib (10 mg) from Preparation Example 1 and orotic acid (3.6 mg), added a mixed solvent of methanol and water (2.5 mL, 3:1), sonicated for dissolution and volatilized at room temperature to obtain the co-crystal Form I of ribociclib and orotic acid in the present invention.

Example 52

Took ribociclib (10 mg) from Preparation Example 1 and orotic acid (3.6 mg), added a mixed solvent of isopropanol and water (3.0 mL, 2:3), sonicated for dissolution and volatilized at room temperature to obtain the co-crystal Form I of ribociclib and orotic acid in the present invention.

Example 53

Took ribociclib (10 mg) from Preparation Example 1 and orotic acid (3.6 mg), added a mixed solvent of acetonitrile and water (1.6 mL, 1:1), sonicated for dissolution and volatilized at 35° C. to obtain the co-crystal Form I of ribociclib and orotic acid in the present invention.

Example 54

Took ribociclib (10 mg) from Preparation Example 1 and orotic acid (3.6 mg), added a mixed solvent of ethanol and acetonitrile (2.5 mL, 2:1), sonicated for dissolution and volatilized at 40° C. to obtain the co-crystal Form I of ribociclib and orotic acid in the present invention.

Example 55

The co-crystal Form I of ribociclib and orotic acid can be obtained by replacing the solvents in Example 54 with the following solvents in the table below.

| Experiment Number | Solvent |
|---|---|
| Experiment 1 | a mixed solvent of dimethyl sulfoxide and water |
| Experiment 2 | a mixed solvent of ethanol and dimethyl sulfoxide |
| Experiment 3 | a mixed solvent of ethyl acetate and methanol |
| Experiment 4 | a mixed solvent of 1,4-dioxane and chloroform |
| Experiment 5 | a mixed solvent of acetone and n-heptane |
| Experiment 6 | a mixed solvent of methanol and isopropyl ether |

Example 56

Took ribociclib (15 mg) from Preparation Example 1 and orotic acid (5.4 mg), added a mixed solvent of methanol and water (0.4 ml, 2:1), heated to 60° C. and stirred for dissolution, cooled to 4° C. at a cooling rate of 5° C./hour, stirred for 1 day, then filtered under reduced pressure. The filter cake was dried at 25° C. under vacuum for 24 hours to obtain the co-crystal Form I of ribociclib and orotic acid in the present invention (18.7 mg).

Example 57

Took ribociclib (15 mg) from Preparation Example 1 and orotic acid (8.1 mg), added a mixed solvent of ethanol and water (1.2 ml, 2:1), heated to 50° C. and stirred for dissolution, cooled to 4° C. at a cooling rate of 8° C./hour, stirred for 2 days, then filtered under reduced pressure. The filter cake was dried at 25° C. under vacuum for 48 hours to obtain the co-crystal Form I of ribociclib and orotic acid in the present invention (17.8 mg).

Example 58

Took ribociclib (15 mg) from Preparation Example 1 and orotic acid (10.8 mg), added a mixed solvent of acetone and water (1.2 ml, 1:1), heated to 55° C. and stirred for dissolution, cooled to room temperature at a cooling rate of 10° C./hour, stirred for 5 days, then filtered under reduced pressure. The filter cake was dried at 40° C. under vacuum for 10 hours to obtain the co-crystal Form I of ribociclib and orotic acid in the present invention (16.5 mg).

Example 59

Took ribociclib (15 mg) from Preparation Example 1 and orotic acid (3.6 mg), added a mixed solvent of 1,4-dioxane and water (0.6 ml, 1:2), heated to 55° C. and stirred for dissolution, cooled to room temperature at a cooling rate of 5° C./hour, stirred for 1 day, then filtered under reduced pressure. The filter cake was dried at 40° C. under vacuum for 24 hours to obtain the co-crystal Form I of ribociclib and orotic acid in the present invention (9.8 mg).

Example 60

The co-crystal Form I of ribociclib and orotic acid can be obtained by replacing the solvents in Example 59 with the following solvents in the table below.

| Experiment Number | Solvent |
|---|---|
| Experiment 1 | Ethanol |
| Experiment 2 | a mixed solvent of dimethyl sulfoxide and acetonitrile |
| Experiment 3 | a mixed solvent of isopropanol and n-heptane |
| Experiment 4 | a mixed solvent of isopropyl acetate and methanol |
| Experiment 5 | a mixed solvent of acetone and dichloromethane |
| Experiment 6 | a mixed solvent of acetone and isopropyl ether |

Example 61

Figure 16:
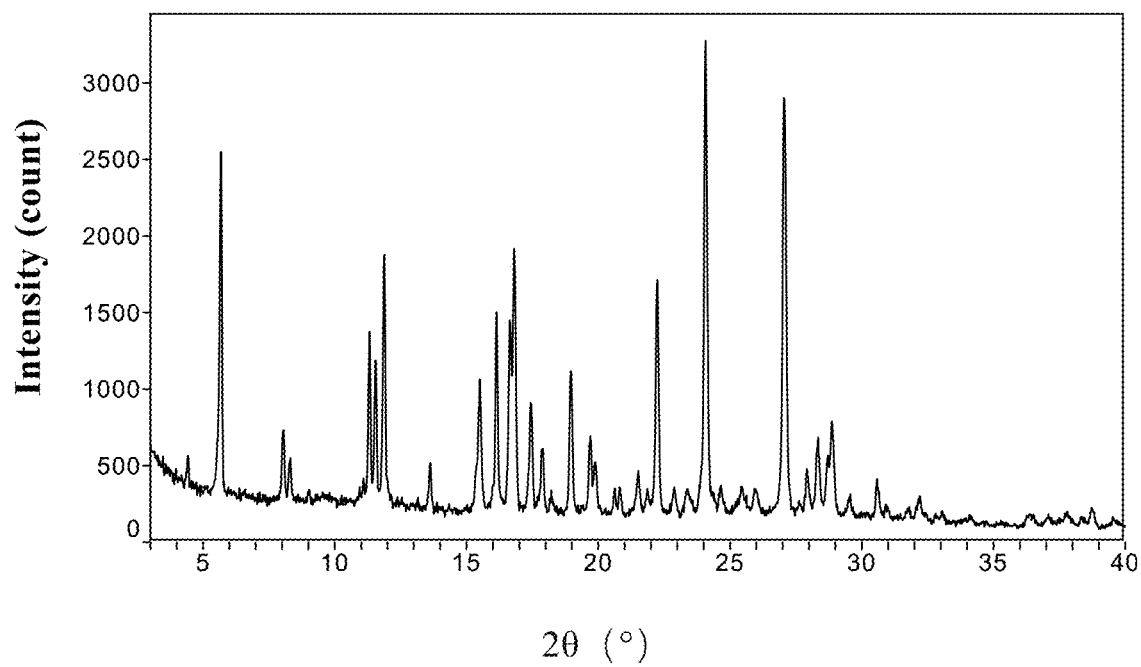
FIG. 16 is the X-ray powder diffraction pattern of the co-crystal Form I of ribociclib and orotic acid in the present invention.
Figure 17:
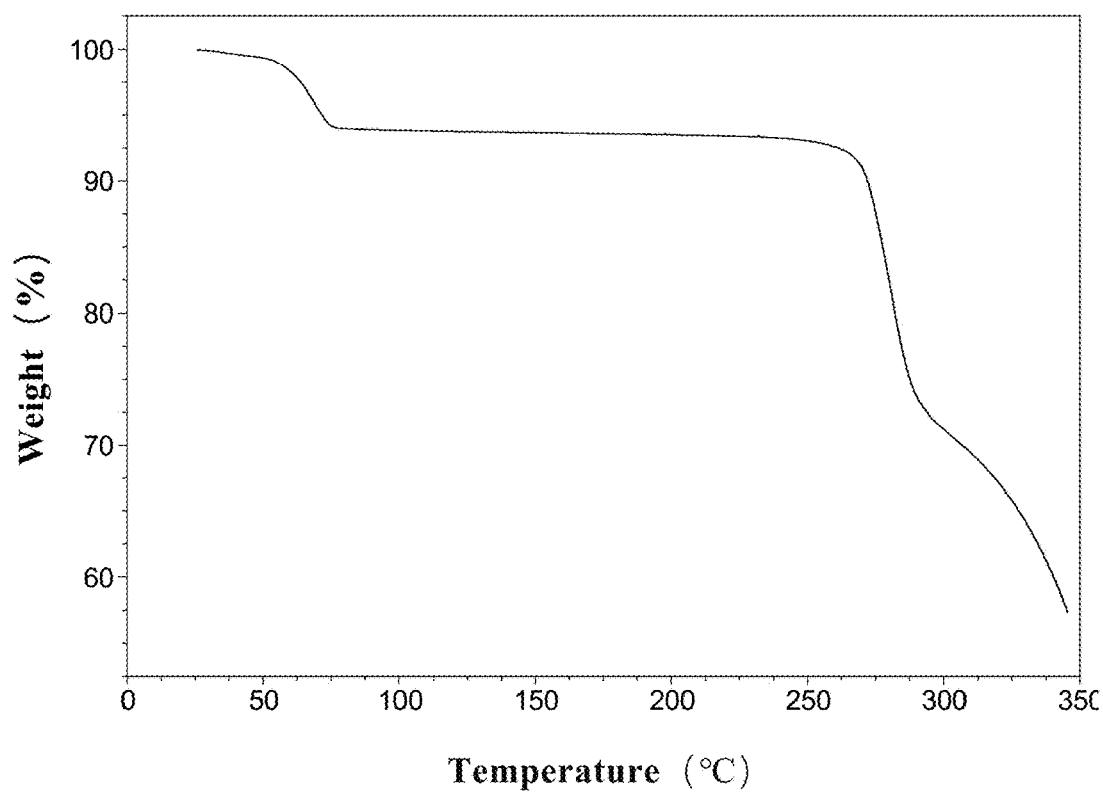
FIG. 17 is the TGA thermogram of the co-crystal Form I of ribociclib and orotic acid in the present invention.
Figure 18:
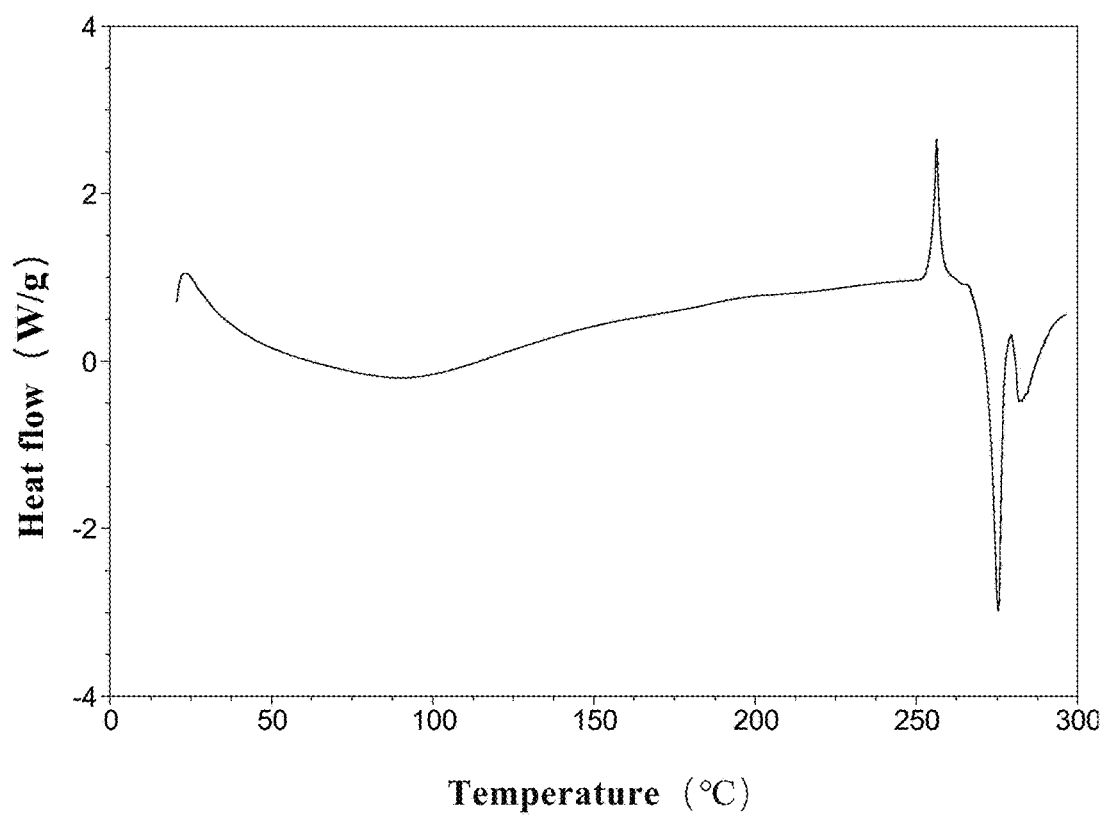
FIG. 18 is the DSC thermogram of the co-crystal Form I of ribociclib and orotic acid in the present invention.
Figure 19:
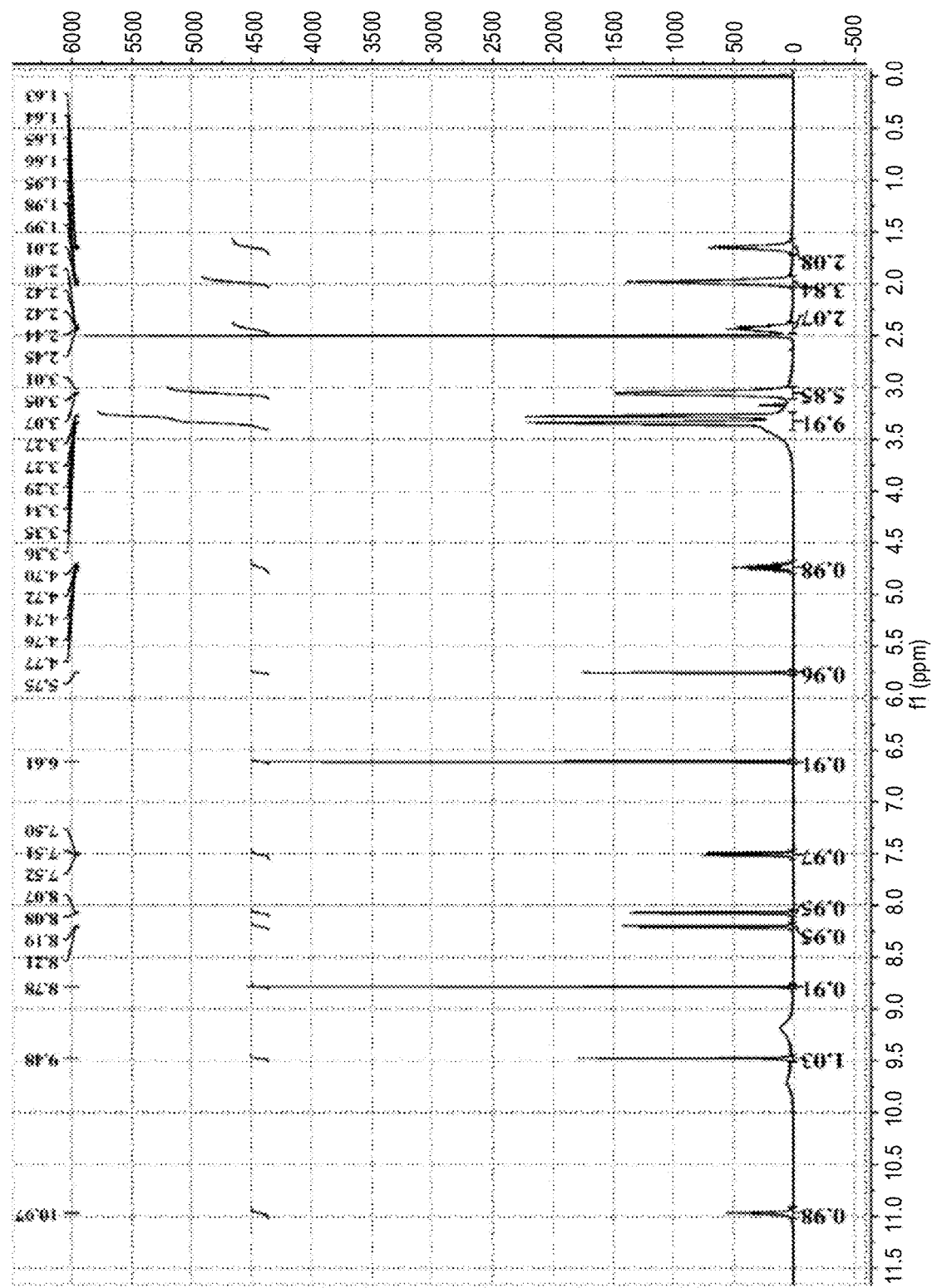
FIG. 19 is the $^1$HNMR spectrum of the co-crystal Form I of ribociclib and orotic acid in the present invention.

The co-crystal Form I of ribociclib and orotic acid obtained from Example 42 was subjected to XRPD characterization. The X-ray powder diffraction pattern is shown in FIG. 16. The TGA thermogram is shown in FIG. 17, showing that it is a hydrate. The DSC thermogram is shown in FIG. 18, showing that the melting point is 272° C. The $^1$HNMR spectrum is shown in FIG. 19, showing that the molar ratio of ribociclib to orotic acid is 1:1.

The samples prepared in Examples 43 to 60 had the same or similar XRPD pattern, DSC thermogram, TGA thermogram and $^1$HNMR spectrum (not shown) as the sample in Example 42. It indicates that the sample in Examples 43 to 60 and the sample in Example 42 have the same co-crystal form.

Example 62

The co-crystal Form I of ribociclib and orotic acid (20 mg) from Example 50 was heated to 60° C. at a rate of 5° C./min, then remained at 65° C. for 10 minutes to obtain the co-crystal Form II of ribociclib and orotic acid.

Figure 20:
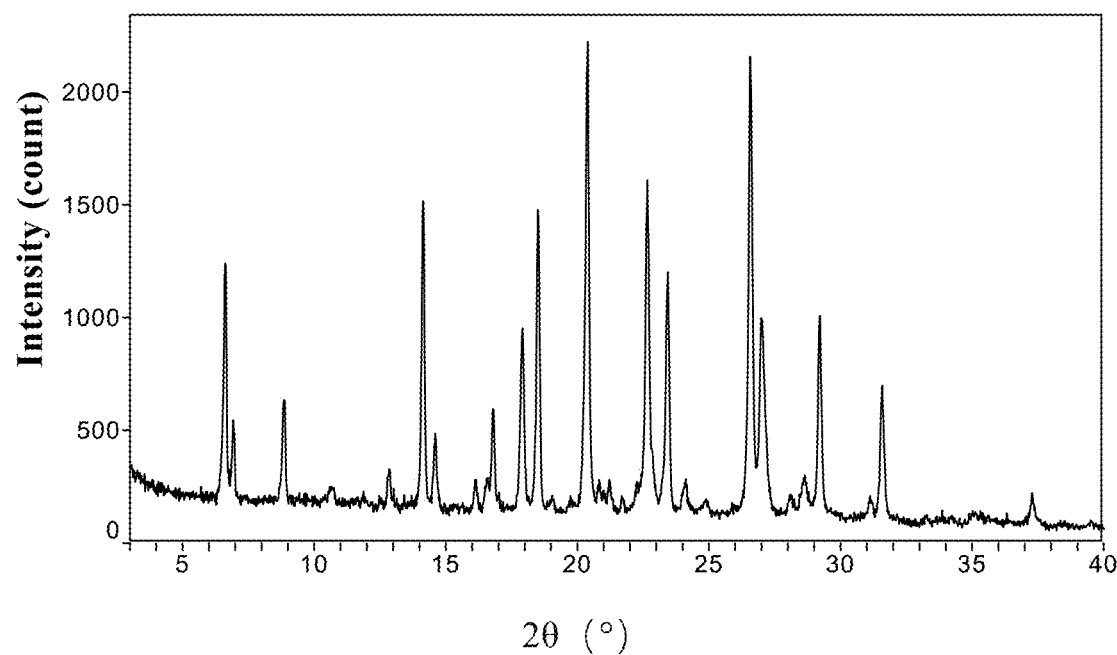
FIG. 20 is the X-ray powder diffraction pattern of the co-crystal Form II of ribociclib and orotic acid in the present invention.

The X-ray powder diffraction pattern is shown in FIG. 20.

Example 63

The co-crystal Form I of ribociclib and orotic acid (20 mg) from Example 50 was heated to 80° C. at a rate of 8° C./min, then remained at 80° C. for 10 minutes to obtain the co-crystal Form II of ribociclib and orotic acid.

Example 64

The co-crystal Form I of ribociclib and orotic acid (25 mg) from Example 50 was heated to 100° C. at a rate of 10° C./min, then remained at 100° C. for 30 minutes to obtain the co-crystal Form II of ribociclib and orotic acid.

The samples prepared in Examples 63 to 64 had the same or similar XRPD pattern as the sample in Example 62. It indicates that the sample in Examples 63 to 64 and the sample in example 62 have the same co-crystal form.

Example 65

Took ribociclib monosuccinate (10 mg) from Preparation Example 2 and citric acid (3.5 mg, 1 equivalent), added methanol (2 mL), sonicated for dissolution and volatilized at room temperature to obtain the co-crystal of ribociclib monosuccinate and citric acid in the present invention.

Example 66

Took ribociclib monosuccinate (10 mg) from Preparation Example 2 and citric acid (3.5 mg, 1 equivalent), added ethanol (10.0 mL), sonicated for dissolution and volatilized at room temperature to obtain the co-crystal of ribociclib monosuccinate and citric acid in the present invention.

Example 67

Took ribociclib monosuccinate (10 mg) from Preparation Example 2 and citric acid (3.5 mg, 1 equivalent), added a mixed solvent of tetrahydrofuran and water (1.0 mL, 1:1), sonicated for dissolution and volatilized at 35° C. to obtain the co-crystal of ribociclib monosuccinate and citric acid in the present invention.

Example 68

Took ribociclib monosuccinate (25 mg) from Preparation Example 2 and citric acid (8.7 mg, 1 equivalent), added a mixed solvent of isopropanol and acetone (1.0 mL, 2:1), sonicated to form a suspension and volatilized at 40° C. to obtain the co-crystal of ribociclib monosuccinate and citric acid in the present invention.

Example 69

Methanol (1.0 mL) and citric acid (17.4 mg, 1 equivalent) were added to ribociclib monosuccinate (50 mg) from Preparation Example 2, stirred at room temperature for 30 hours, then filtered under reduced pressure. The filter cake was dried at 40° C. under vacuum for 10 hours to obtain the co-crystal of ribociclib monosuccinate and citric acid in the present invention (64.1 mg).

Example 70

A mixed solvent of ethyl acetate and tetrahydrofuran (2.5 mL, 1:1) citric acid (26.1 mg, 1.5 equivalents) were added to ribociclib monosuccinate (50 mg) from Preparation Example 2, stirred at room temperature for 24 hours, then filtered under reduced pressure. The filter cake was dried at 25° C. under vacuum for 24 hours to obtain the co-crystal of ribociclib monosuccinate and citric acid in the present invention (63.3 mg).

Example 71

A mixed solvent of methanol and acetone (2.0 mL, 1:1) citric acid (34.8 mg, 2 equivalents) were added to ribociclib monosuccinate (50 mg) from Preparation Example 2, stirred at room temperature for 72 hours, then filtered under reduced pressure. The filter cake was dried at 30° C. under vacuum for 20 hours to obtain the co-crystal of ribociclib monosuccinate and citric acid in the present invention (63.5 mg).

Example 72

A mixed solvent of water and acetonitrile (2.0 mL, 1:1) citric acid (17.4 mg, 1 equivalent) were added to ribociclib monosuccinate (50 mg) from Preparation Example 2, stirred at 40° C. for 8 hours, then filtered under reduced pressure. The filter cake was dried at 40° C. under vacuum for 36 hours to obtain the co-crystal of ribociclib monosuccinate and citric acid in the present invention (53.6 mg).

Example 73

Acetone (0.5 mL) was added to ribociclib monosuccinate (50 mg) from Preparation Example 2 and citric acid (8.7 mg, 0.5 equivalent). After the mixture was completely wetted with acetone at room temperature, then ground to dryness to obtain the co-crystal of ribociclib monosuccinate and citric acid in the present invention.

Example 74

Methanol (0.5 mL) was added to ribociclib monosuccinate (30 mg) from Preparation Example 2 and citric acid (10.4 mg, 1 equivalent). After the mixture was completely wetted with methanol at room temperature, then ground to dryness to obtain the co-crystal of ribociclib monosuccinate and citric acid in the present invention.

Example 75

Dichloromethane (0.6 mL) was added to ribociclib monosuccinate (30 mg) from Preparation Example 2 and citric acid (20.9 mg, 2 equivalents). After the mixture was completely wetted with dichloromethane at 40° C., then ground to dryness to obtain the co-crystal of ribociclib monosuccinate and citric acid in the present invention.

Example 76

Tetrahydrofuran (0.4 mL) was added to ribociclib monosuccinate (30 mg) from Preparation Example 2 and citric acid (10.4 mg, 1 equivalent). After the mixture was completely wetted with tetrahydrofuran at 40° C., then ground to dryness to obtain the co-crystal of ribociclib monosuccinate and citric acid in the present invention.

Example 77

Took ribociclib monosuccinate (15 mg) from Preparation Example 2 and citric acid (5.2 mg, 1 equivalent), added a mixed solvent of tetrahydrofuran and methanol (1.5 mL, 1:1), heated to 55° C. and stirred for dissolution, cooled to 4° C. at a cooling rate of 5° C./hour, then filtered under reduced pressure. The filter cake was dried at 25° C. under vacuum for 24 hours to obtain the co-crystal of ribociclib monosuccinate and citric acid in the present invention (12.5 mg).

Example 78

Took ribociclib monosuccinate (15 mg) from Preparation Example 2 and citric acid (7.8 mg, 1.5 equivalents), added a mixed solvent of acetone and water (0.5 mL, 1:2), heated to 60° C. and stirred for dissolution, cooled to 6° C. at a cooling rate of 8° C./hour, then filtered under reduced pressure. The filter cake was dried at 25° C. under vacuum for 48 hours to obtain the co-crystal of ribociclib monosuccinate and citric acid in the present invention (11.8 mg).

Example 79

Took ribociclib monosuccinate (15 mg) from Preparation Example 2 and citric acid (10.4 mg, 2 equivalents), added a mixed solvent of isopropanol and tetrahydrofuran (1.5 mL, 4:1), heated to 65° C. and stirred for dissolution, cooled to room temperature at a cooling rate of 10° C./hour, then filtered under reduced pressure. The filter cake was dried at 40° C. under vacuum for 10 hours to obtain the co-crystal of ribociclib monosuccinate and citric acid in the present invention (10.9 mg).

Example 80

Took ribociclib monosuccinate (50 mg) from Preparation Example 2 and citric acid (17.4 mg, 1 equivalent), added a mixed solvent of ethanol and dimethyl sulfoxide (1 mL, 4:1), heated to 60° C. and stirred for dissolution, cooled to room temperature at a cooling rate of 6° C./hour, then filtered under reduced pressure. The filter cake was dried at 40° C. under vacuum for 24 hours to obtain the co-crystal of ribociclib monosuccinate and citric acid in the present invention (37 mg).

Example 81

The co-crystal of ribociclib mono-succinate and citric acid can be obtained by replacing the solvents in Example 66, Example 70, Example 75 and Example 79 with the following solvents in the table below.

| Experiment Number | Solvent |
| --- | --- |
| Experiment 1 | acetone/isobutyl acetate |
| Experiment 2 | sec-butanol |
| Experiment 3 | tetrahydrofuran/methyl tert-butyl ether |
| Experiment 4 | n-propanol/isopropyl ether |
| Experiment 5 | ethanol/n-heptane |
| Experiment 6 | trifluoroethanol/cyclohexane |

Example 82

Figure 21:
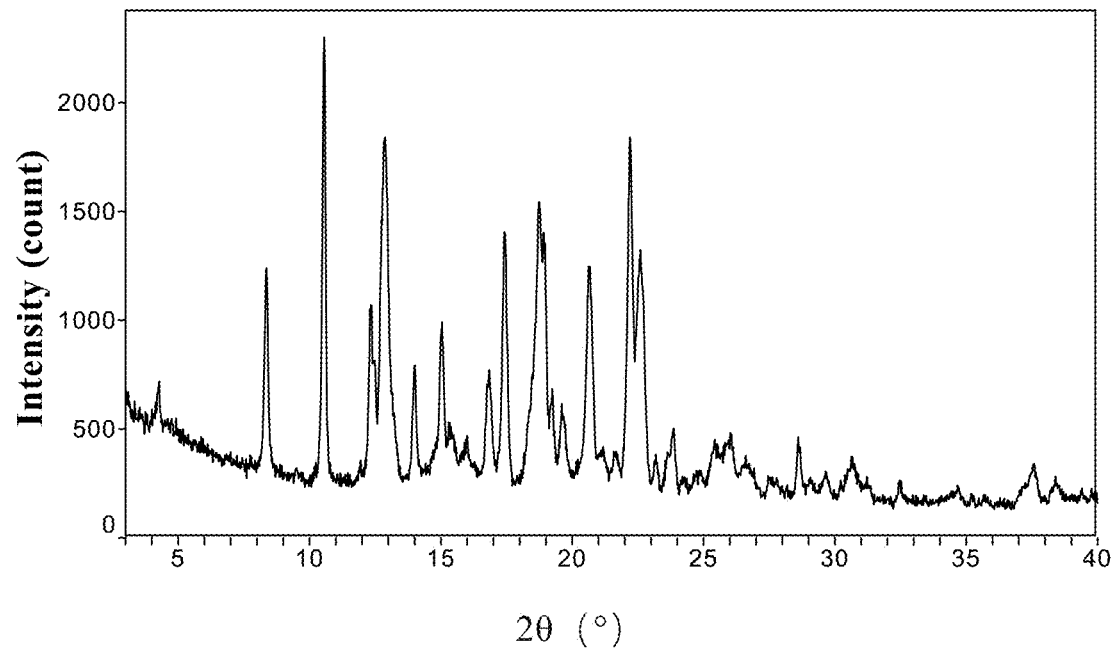
FIG. 21 is the X-ray powder diffraction pattern of the co-crystal of ribociclib monosuccinate and citric acid in the present invention.

The co-crystal of ribociclib monosuccinate and citric acid obtained from Example 65 was subjected to XRPD characterization. The X-ray powder diffraction pattern is shown in FIG. 21.

Figure 22:
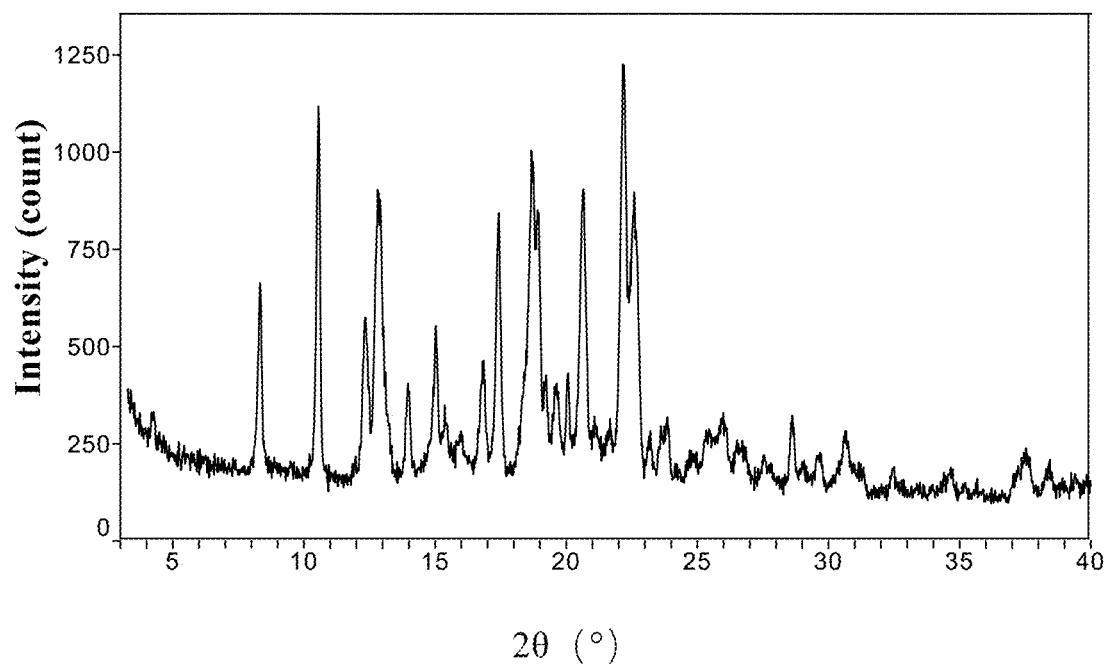
FIG. 22 is the X-ray powder diffraction pattern of the co-crystal of ribociclib monosuccinate and citric acid in the present invention.
Figure 23:
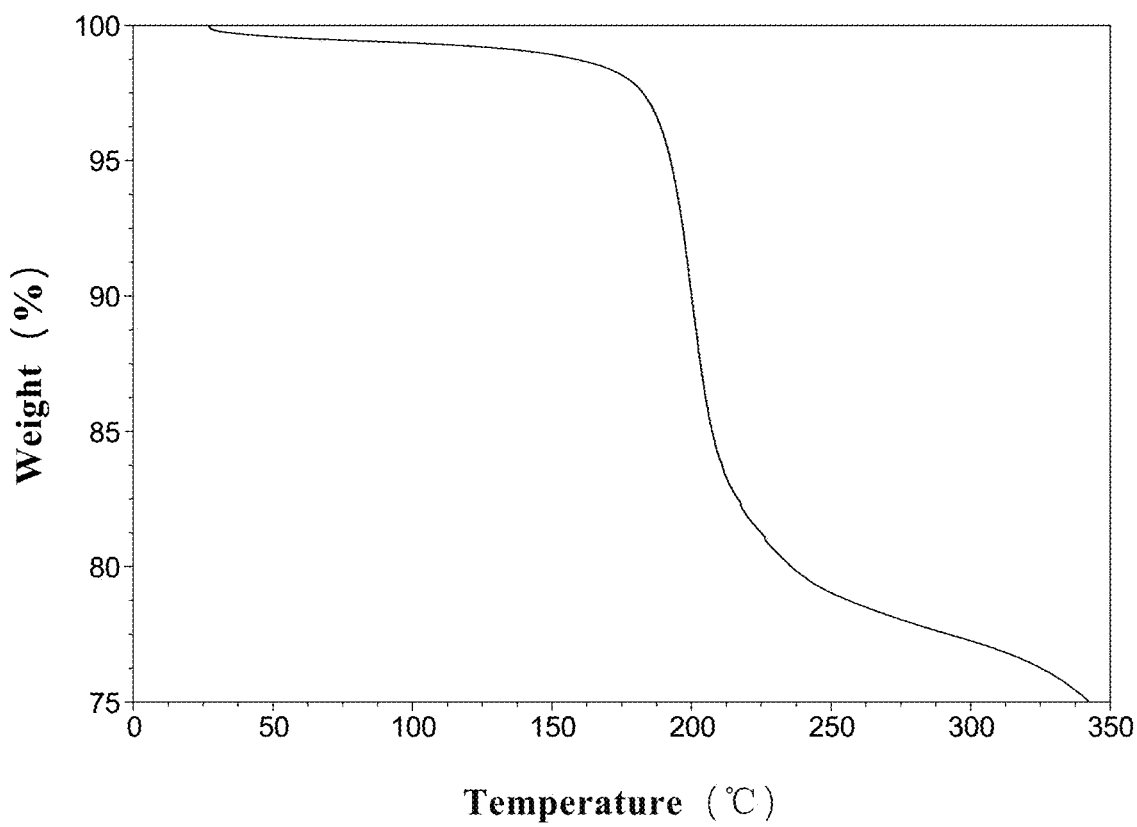
FIG. 23 is the TGA thermogram of the co-crystal of ribociclib monosuccinate and citric acid in the present invention.
Figure 24:
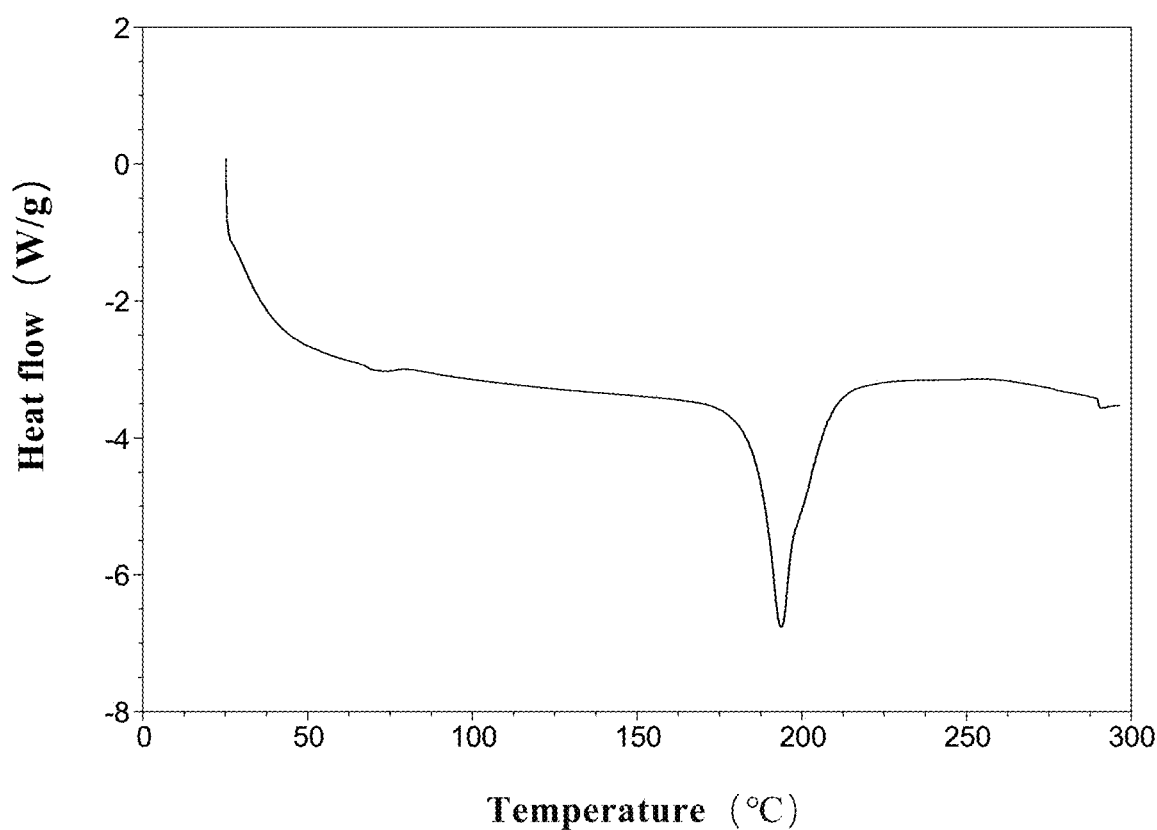
FIG. 24 is the DSC thermogram of the co-crystal of ribociclib monosuccinate and citric acid in the present invention.
Figure 25:
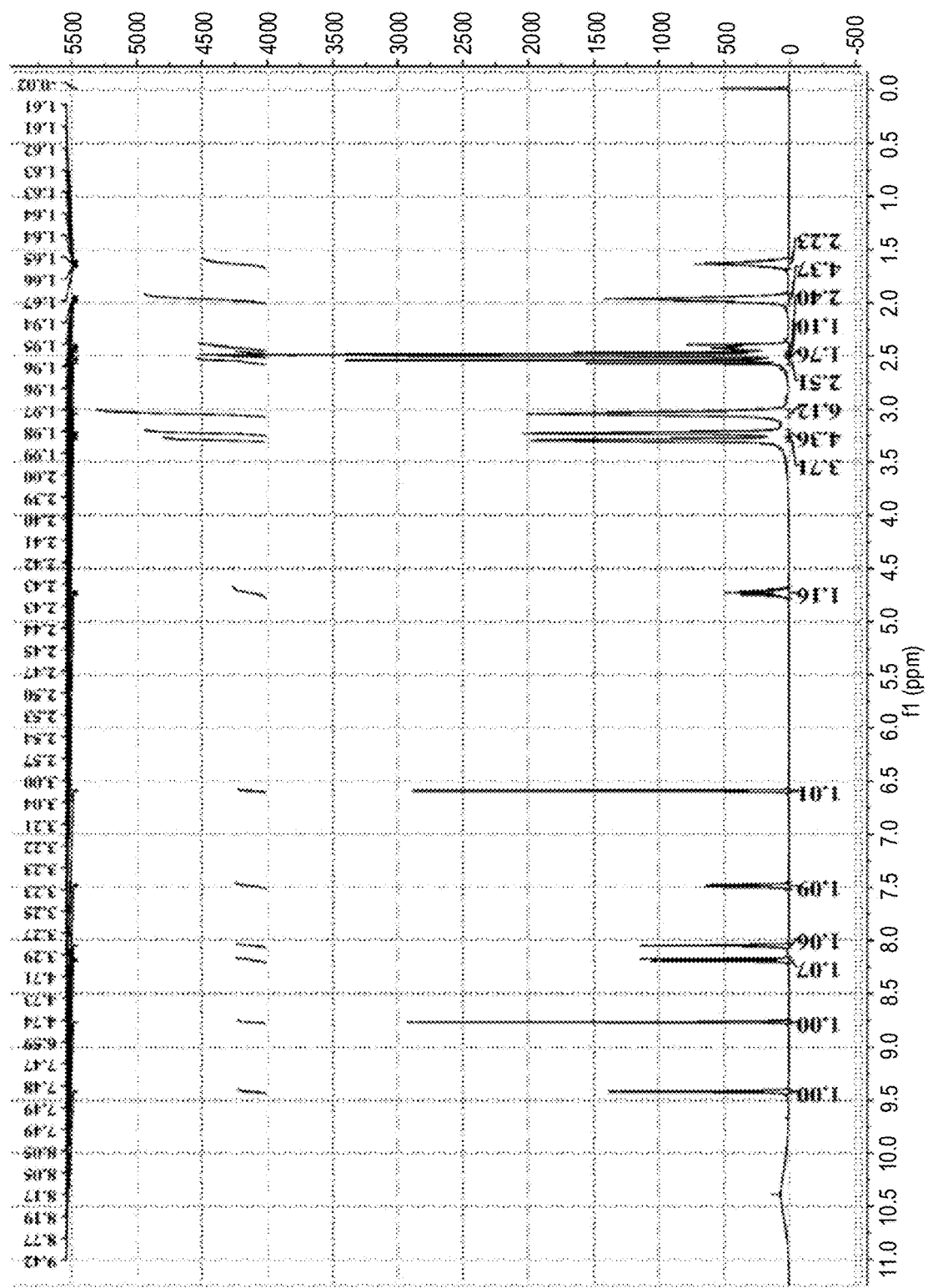
FIG. 25 is the ¹HNMR spectrum of co-crystal of the ribociclib monosuccinate and citric acid in the present invention.

The co-crystal of ribociclib monosuccinate and citric acid obtained from Example 69 was subjected to characterization. The X-ray powder diffraction pattern is shown in FIG. 22. The TGA thermogram is shown in FIG. 23, showing that it is an anhydrate. The DSC thermogram is shown in FIG. 24, showing that the melting point is 186° C. The $^1$HNMR spectrum is shown in FIG. 25, showing that the molar ratio of ribociclib monosuccinate to citric acid is 1:1.

The samples prepared in Examples 66 to 81 had the same or similar XRPD pattern, DSC thermogram, TGA thermogram and HNMR spectrum as the samples in Example 65 and Example 69. It indicates that the samples in Examples 65 to 81 are the same co-crystal compound.

Example 83

Tablet: a large number of tablets were prepared by conventional process. The dosage unit contains 200 mg of the active ingredient (284 mg of the co-crystal form of ribociclib and saccharin in the present invention), 10 mg of silicon dioxide, 10 mg of magnesium stearate, 245 mg of microcrystalline cellulose, 10 mg of cross-linked povidone and 25 mg of hydroxypropyl cellulose. Appropriate aqueous or non-aqueous coating can be used to increase palatability, improve appearance and stability, or delay absorption.

Example 84

Tablet: The co-crystal of ribociclib and saccharin in Example 83 was replaced with the co-crystal From I or Form II of ribociclib and cholic acid, or the co-crystal From I or Form II of ribociclib and orotic acid in present invention, or the co-crystal of ribociclib monosuccinate and citric acid. The free bases in the co-crystals of the formulation have the same molar amount as the free base in the co-crystal of ribociclib and saccharin, and the total amount of the co-crystal and the fillers in the formulation is the same as Example 83, and other preparation steps are the same as those in the Example 83.

Example 85

Hard shell capsule: a large number of capsules was prepared by filling a traditional two-piece hard capsules. The dosage unit contains 200 mg of powdered active ingredient (284 mg of the co-crystal of ribociclib and saccharin in the present invention), 8 mg of silicon dioxide, 8 mg of magnesium stearate, 156 mg of microcrystalline cellulose, 8 mg of cross-linked povidone and 20 mg of hydroxypropyl cellulose.

Example 86

Hard shell capsule: The co-crystal of ribociclib and saccharin in Example 85 was replaced with the co-crystal From I or Form II of ribociclib and cholic acid, or the co-crystal From I or Form II of ribociclib and orotic acid in present invention, or the co-crystal of ribociclib monosuccinate and citric acid. The free bases in the co-crystals of the formulation and in the co-crystal of ribociclib and saccharin have the same molar amount, and the total amount of the co-crystal and the fillers in the formulation is the same as Example 85, and other preparation steps are the same as those in the Example 85.

Example 87

Soft gelatin capsule: The mixture of active ingredient was prepared in digestible oils such as soybean oil, cottonseed oil or olive oil. Molten gelatin was pumped by active displacement pump to form soft gelatin capsules containing 200 mg active ingredient (284 mg of the co-crystal form of ribociclib and saccharin). The capsules were washed and dried. The active ingredient can be dissolved in a mixture of polyethylene glycol, glycerin and sorbitol to prepare a water-compatible pharmaceutical mixture.

Example 88

Soft gelatin capsule: The co-crystal of ribociclib and saccharin of Example 87 was replaced with the co-crystal Form I or Form II of ribociclib and cholic acid in present invention, or the co-crystal From I or Form II of ribociclib and orotic acid in present invention, or the co-crystal from of ribociclib monosuccinate and citric acid. The free bases in the co-crystals of the formulation and in the co-crystal of ribociclib and saccharin have the same molar amount, and the total amount of the co-crystal and the fillers in the formulation is the same as Example 87, and other preparation steps are the same as those in the Example 87.

Example 89

Immediate release tablet/capsule: This solid oral dosage form was prepared by conventional and new processes. These dosage units are taken orally and rapidly break down. The active ingredient (the co-crystal of ribociclib and saccharin) was mixed with liquids containing such as sugar, gelatin, pectin and sweetener. These liquids were solidified into solid tablets or caplets by freeze-drying and solid extraction techniques. The pharmaceutical compounds can be compressed with viscoelastic and thermoelastic sugars and polymers or effervescent ingredients to produce a porous matrix for rapid release that does not require water.

Example 90

Immediate release tablet/capsule: The co-crystal of ribociclib and saccharin of Example 89 was replaced with the co-crystal Form I or Form II of ribociclib and cholic acid in present invention, or the co-crystal From I or Form II of ribociclib and orotic acid acid in present invention, or the co-crystal of ribociclib monosuccinate and citric acid. The free bases in the co-crystals of the formulation and in the co-crystal of ribociclib and saccharin have the same molar amount, and the total amount of the co-crystal and the fillers in the formulation is the same as Example 89, and other preparation steps are the same as those in the Example 89.

Example 91

Sustained-release tablet/capsule: This kind of solid oral dosage form was prepared by conventional and new processes. These dosage units are taken orally to release slowly and deliver the drug. The active ingredient (the co-crystal of ribociclib and saccharin) was mixed with one or more solids such as starch, sugar or other hygroscopic agent, prepared into solid dispersion by aqueous hypromellose solution or by ethylcellulose ethanol solution, then prepared into solid tablets or caplets by wet granulation.

Example 92

Sustained-release tablet/capsule: The co-crystal of ribociclib and saccharin of Example 91 was replaced with the co-crystal Form I or Form II of ribociclib and cholic acid in present invention, or the co-crystal From I or Form II of ribociclib and orotic acid acid in present invention, or the co-crystal of ribociclib mono-succinate and citric acid. The free bases in the co-crystals of the formulation and in the co-crystal of ribociclib and saccharin have the same molar amount, and the total amount of the co-crystal and the fillers in the formulation is the same as Example 91, and other preparation steps are the same as those in the Example 91.

Example 93

Sterile IV solution: The co-crystal of ribociclib and saccharin in present invention was formulated into a 2.5 mg/mL solution with sterile water for injection, meanwhile 2 wt % of solubilizer Pluronic F-68 was adjust the pH value as needed. For administration, the above solution was diluted with 5% sterile dextrose to 0.5 to 2.5 mg/mL and administered as an intravenous infusion over 10 to 30 minutes.

Example 94

Sterile IV solution: The co-crystal of ribociclib and saccharin of Example 93 was replaced with the co-crystal Form I or Form II of ribociclib and cholic acid in present invention, or the co-crystal From I or Form II of ribociclib and orotic acid in present invention, or the co-crystal of ribociclib mono-succinate and citric acid. The free bases in the co-crystals of the formulation and in the co-crystal of ribociclib and saccharin have the same molar amount, and the total amount of the co-crystal and the fillers in the formulation is the same as Example 93, and other preparation steps are the same as those in the Example 93.

Example 95

Lyophilized powder for intravenous administration: This kind of sterile formulation may contain (i) 135-1350 mg of the lyophilized powder of the co-crystal of ribociclib and saccharin in present invention, (ii) 32-327 mg/mL of sodium citrate, and (iii) 32-327 mg of dextran 40. The co-crystal of ribociclib and saccharin in present invention was formulated into a solution of 6 mg/mL to 13 mg/mL with the sterile water for injection or 5% dextran solution, then diluted with saline or 5% dextrose solution to reach the concentration of 0.1 mg/mL to 0.6 mg/mL, and administrated by intravenous bolus or intravenous infusion for 10 to 30 minutes.

Example 96

Lyophilized powder for intravenous administration: The co-crystal form of ribociclib and saccharin of Example 95 was replaced with the co-crystal Form I or Form II of ribociclib and cholic acid in present invention, or the co-crystal From I or Form II of ribociclib and orotic acid in present invention, or the co-crystal of ribociclib monosuccinate and citric acid. The free bases in the co-crystals of the formulation and in the co-crystal of ribociclib and saccharin have the same molar amount, and the total amount of the co-crystal and the fillers in the formulation is the same as Example 95, and other preparation steps are the same as those in the Example 95.

Example 97

Intramuscular suspension: For intramuscular injection, the following solutions or suspensions can contain.
1 mg/mL of the co-crystal ribociclib and saccharin (water-insoluble compounds).
0.5 mg/mL of sodium carboxymethyl cellulose.
0.1 mg/mL of Tween80.
9 mg/mL of sodium chloride.
9 mg/m of benzyl alcohol.

Example 98

Intramuscular suspension: The co-crystal of ribociclib and saccharin of Example 97 was replaced with the co-crystal Form II of ribociclib and cholic acid in present invention, or the co-crystal From I or Form II of ribociclib and orotic acid in present invention, or the co-crystal of ribociclib monosuccinate and citric acid. The free bases in the co-crystals of the formulation and in the co-crystal of ribociclib and saccharin have the same molar amount, and the total amount of the co-crystal and the fillers in the formulation is the same as Example 97, and other preparation steps are the same as those in the Example 97.

Comparative Example 1

The co-crystal Form III of ribociclib and MEK prepared in Preparation Example 3, the co-crystal of ribociclib and saccharin in present invention, and the co-crystal form of ribociclib monosuccinate and citric acid in present invention were subjected to crystal stability test. The specific operations were as follows: 10 mg of above samples were respectively placed at 80° C. for 24 hours, then subjected to crystal form detection by XPRD.

TABLE 1

The research of crystal stability after having been placed for 24 hours.

| Sample | Crystal Form |
|---|---|
| The known co-crystal From III of ribociclib and MEK | Changed (appearance of new diffraction peaks) |
| The co-crystal of ribociclib and saccharin in present invention | Unchanged |
| The co-crystal of ribociclib monosuccinate and citric acid in present invention | Unchanged |

As shown in Table 1, the co-crystal of ribociclib and saccharin has better crystal stability than the co-crystal Form III of ribociclib and MEK.

Comparative Example 2

The co-crystal Form III of ribociclib and MEK162 prepared according to Preparation Example 3, the co-crystal form of ribociclib and saccharin in the present invention, the co-crystal Form I of ribociclib and cholic acid in the present invention, the co-crystal Form I of ribociclib and orotic acid in the present invention and the co-crystal of ribociclib monosuccinate and citric acid in present invention were subjected to water solubility test. The specific operations were as follows: 10 mg of above samples were respectively added to a 20 mL glass bottle, followed by addition of 10 mL of deionized water, then sonicated at 25° C. for 1 minute; some sample was taken and filtered for HPLC detection; and the sample solubility in water was calculated.

TABLE 2

The apparent water solubility.

| Sample | Solubility (ug/mL) |
|---|---|
| The known co-crytal Form III of ribocicliband MEK 162 | 2.6 |
| The co-cryatal of ribociclib and saccharin in the present invention | About 100 |
| The co-cryatal Form I of ribociclib and cholic acid in the present invention | 100 |
| The co-cryatal Form I of ribociclib and orotic acid in thepresent invention | 110 |
| The co-cryatal of ribociclib monosuccinate and citric acid in the present invention | 50000 |

The results show that the phases of Crystalline Form of Compound A and Crystalline Form of Compound B in the present invention are unchanged after having been stored at room temperature and high temperature for 14 days, and have good crystal stability.

As shown in Table 2, the solubility of the co-crystal Form I of ribociclib and cholic acid, and the co-crystal Form I of ribociclib and orotic acid in the present invention is higher 30 to 50 times than the co-crystal Form III of ribociclib and MEK. The solubility of the co-crystal form of ribociclib monosuccinate and citric acid in the present invention is higher 20000 times than the co-crystal Form III of ribociclib and MEK. It indicates that the co-crystal Form I of ribociclib and cholic acid, the co-crystal Form I of ribociclib and orotic acid, and the co-crystal of ribociclib monosuccinate and citric acid have better solubility and better bioavailability.

Comparative Example 3

The crystal Form I ribociclib monosuccinate prepared according to the Preparation Example 2 and the co-crystal of ribociclib monosuccinate and citric acid were subjected to stability test in water. The specific operations were as follows: 100 mg of above samples were respectively added to a 5 mL glass bottle, followed by addition of 5 mL of deionized water, placed and stirred at 25° C. for 24 hours; some sample was taken and filtered, then subjected to crystal form detection by XPRD.

TABLE 3

The solubility in water.

| Sample | Crystal Form |
|---|---|
| Theknown crystal Form I of ribociclib monosuccinate | Changed (appearnce of new diffraction peaks) |
| The co-crystal of ribociclib monosuccinateand citric acidin the present invention | Unchanged |

As shown in Table 3, compared with the known crystal Form I of ribociclib monosuccinate, the co-crystal of ribociclib monosuccinate and citric acid in the present invention has higher stability in water, thus has better formulation processability and bioavailability.

All patents, patent application publications, patent applications and non-patent publications cited in this specification are hereby incorporated by reference in their entireties.

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subjected to the scope of protection defined in the claims.

What is claimed is:

1. A co-crystal of ribociclib and saccharin with the following formula (I),

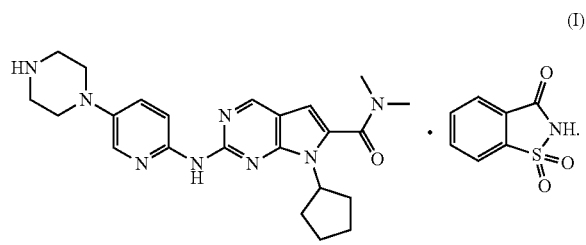

2. The co-crystal of ribociclib and saccharin according to claim 1, wherein the co-crystal is in a crystalline form of an anhydrate, a hydrate, or a non-solvate.

3. The co-crystal of ribociclib and saccharin according to claim 2, wherein the X-ray powder diffraction pattern of the co-crystal, expressed as 2θ angles, has the following characteristic peaks: 8.4°±0.2°, 10.2°±0.2°, 12.7°±0.2°, 17.7°±0.2°, 21.0°±0.2° and 22.7°±0.2°.

4. A pharmaceutical composition comprising a therapeutically effective amount of the co-crystal of ribociclib and saccharin according to claim 1 and at least one pharmaceutically acceptable carrier.

5. A method of preparing the co-crystal of ribociclib and saccharin according to claim 1, the method comprising reacting ribociclib with one molar equivalent to two molar equivalents of saccharin; wherein the reacting is in an organic solvent or in combined organic solvents; and wherein the organic solvent is a solvent capable of dissolving ribociclib or saccharin.

6. A method of preparing the co-crystal of ribociclib and saccharin according to claim 3, the method comprising:
mixing ribociclib, saccharin, and a solvent, and crystallizing to obtain the co-crystal of ribociclib and saccharin; wherein the solvent is selected from the group consisting of methanol, ethanol, isopropanol, ethyl acetate, dichloromethane, tetrahydrofuran, 1,4-dioxane, acetone, acetonitrile, dimethylsulfoxide, water, and any combination thereof; and wherein:
(1) the method is a volatilization method;
the molar ratio of ribociclib to saccharin is 1:1;
the solvent is selected from the group consisting of methanol, ethanol, acetone, acetonitrile, ethyl acetate, water, and any combination thereof;
the volatilization method is performed at 10° C. to 40° C.; and
the mass-volume ratio of ribociclib to the solvent ranges from 1 mg/mL to 25 mg/mL;
(2) the method is a slurry method;
the molar ratio of ribociclib to saccharin ranges from 1:1 to 1:2;
the solvent is selected from the group consisting of methanol, ethanol, isopropanol, acetonitrile, tetrahydrofuran, water, and any combination thereof;
the slurry method is performed at 10° C. to 40° C.;
the duration for reaction ranges from 8 to 72 hours; and
the mass-volume ratio of ribociclib to the solvent ranges from 25 mg/mL to 50 mg/mL;
(3) the method is a solid grinding method;
the molar ratio of ribociclib to saccharin ranges from 1:0.5 to 1:2;
the solvent is selected from the group consisting of methanol, acetone, tetrahydrofuran, dichloromethane, water, and any combination thereof;
the mass-volume ratio of ribociclib and saccharin, to the solvent ranges from 50 mg/mL to 100 mg/mL; and
the solid grinding method is performed at 10° C. to 40° C.; or
(4) the method is a cooling crystallization method; the starting point temperature ranges from 50° C. to 60° C.;
the molar ratio of ribociclib to saccharin ranges from 1:1 to 1:2;
the solvent is selected from the group consisting of methanol, ethanol, acetone, 1,4-dioxane, water, and any combination thereof;
the ending point temperature ranges from 0° C. to 30° C.;
the cooling rate ranges from 5 to 10° C./hour; and
the mass-volume ratio of ribociclib to the solvent ranges from 10 mg/mL to 50 mg/mL.

7. A co-crystal of ribociclib and cholic acid with the following formula (II),

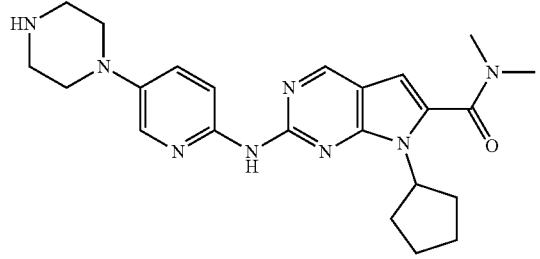
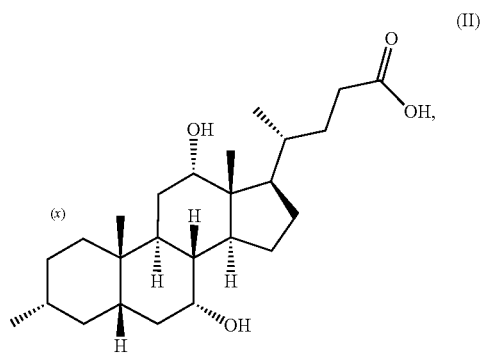

wherein x is 1; and wherein the co-crystal is in a crystalline form of an anhydrate, a hydrate, or a non-solvate.

8. The co-crystal of ribociclib and cholic acid according to claim 7, wherein the crystalline form is co-crystal Form I of ribociclib and cholic acid.

9. The co-crystal Form I of ribociclib and cholic acid according to claim 8, wherein the X-ray powder diffraction pattern of the co-crystal Form I, expressed as 2θ angles, has one or more of the following characteristic peaks:
4.6°±0.2°, 9.1°±0.2°, 10.9°±0.2° and 15.9°±0.2°.

10. A pharmaceutical composition comprising a therapeutically effective amount of the co-crystal of ribociclib and cholic acid according to claim 7 and at least one pharmaceutically acceptable carrier.

11. A method of preparing the co-crystal of ribociclib and cholic acid according to claim 8, the method comprising reacting ribociclib with one molar equivalent to two molar equivalents of cholic acid, wherein the reacting is in an organic solvent solution or in a mixed organic solvent solution; and wherein the organic solvent is a solvent capable of dissolving ribociclib or cholic acid.

12. A method of preparing the co-crystal of ribociclib and cholic acid according to claim 8, the method comprising:
mixing ribociclib, cholic acid, and a solvent, and removing the solvent after reaction to obtain the co-crystal of ribociclib and cholic acid; wherein the solvent is selected from the group consisting of methanol, ethanol, isopropanol, ethyl acetate, dichloromethane, tetrahydrofuran, 1,4-dioxane, acetone, acetonitrile, dimethylsulfoxide, water and any combination thereof;

and wherein:

(1) the method is a slurry method;
the solvent is selected from the group consisting of methanol, ethanol, acetone, acetonitrile, tetrahydrofuran, water and any combination thereof;
the molar ratio of ribociclib to cholic acid ranges from 1:1 to 1:2;
the slurry method is performed at 10° C. to 40° C.;
the duration for crystallization ranges from 8 to 72 hours;
the mass-volume ratio of ribociclib to the solvent ranges from 10 mg/mL to 50 mg/mL; and
the mass-volume ratio of cholic acid to the solvent ranges from 10 mg/mL to 65 mg/mL;

(2) the method is a solid grinding method;
the solvent is selected from the group consisting of methanol, ethanol, tetrahydrofuran, dichloromethane, water and any combination thereof;
the mass-volume ratio of ribociclib and cholic acid, to the solvent ranges from 27 mg/mL to 100 mg/mL; and
the solid grinding method is performed at 10° C. to 40° C.;

(3) the method is a volatilization method;
the solvent is selected from the group consisting of methanol, ethanol, isopropanol, ethyl acetate, acetonitrile, water and any combination thereof;
the volatilization method is performed at 10° C. to 40° C.; and
the mass-volume ratio of ribociclib and cholic acid, to the solvent ranges from 3 mg/mL to 20 mg/mL; or (4) the method is a cooling crystallization method;
the molar ratio of ribociclib to cholic acid ranges from 1:1 to 1:2;
the solvent is selected from the group consisting of methanol, ethanol, acetone, 1,4-dioxane, water and any combination thereof;
the crystallization temperature is from 0° C. to 30° C.;
the cooling rate ranges from 5 to 10° C./hour; and
the mass-volume ratio of ribociclib and cholic acid, to the solvent ranges from 19 mg/mL to 60 mg/mL.

13. A co-crystal of ribociclib and orotic acid with the following formula (III),

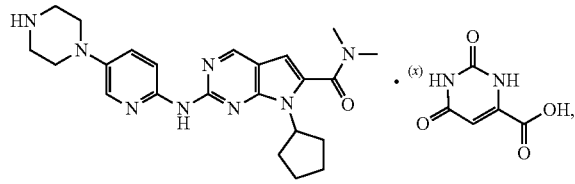

(III)

wherein x is 1; and wherein the co-crystal is in a crystalline form of an anhydrate, a hydrate, or a non-solvate.

14. The co-crystal of ribociclib and orotic acid according to claim 13, wherein the crystalline form is co-crystal Form I of ribociclib and orotic acid.

15. The co-crystal Form I of ribociclib and orotic acid according to claim 14, wherein the X-ray powder diffraction pattern of the co-crystal Form I, expressed as 2θ angles, has one or more of the following characteristic peaks:
5.7°±0.2°, 16.8°±0.2°, 22.2°±0.2° and 24.1°±0.2°.

16. A pharmaceutical composition comprising a therapeutically effective amount of the co-crystal of ribociclib and orotic acid according to claim 13 and at least one pharmaceutically acceptable carrier.

17. A method of preparing the co-crystal of ribociclib and orotic acid according to claim 14, the method comprising reacting ribociclib with one molar equivalent to two molar equivalents of orotic acid, wherein the reacting is in an organic solvent or in combined organic solvents; and wherein the organic solvent is a solvent capable of dissolving ribociclib or orotic acid.

18. A method of preparing the co-crystal of ribociclib and orotic acid according to claim 14, the method comprising:
mixing ribociclib, orotic acid, and a solvent, and removing the solvent after reaction to obtain the co-crystal of ribociclib and orotic acid; wherein the solvent is selected from the group consisting of methanol, ethanol, isopropanol, ethyl acetate, dichloromethane, tetrahydrofuran, 1,4-dioxane, acetone, acetonitrile, dimethylsulfoxide, water and any combination thereof; and wherein:

(1) the method is a slurry method;
the solvent is selected from the group consisting of methanol, ethanol, acetone, acetonitrile, tetrahydrofuran, water and any combination thereof;
the molar ratio of ribociclib to orotic acid ranges from 1:1 to 1:2;
the slurry method is performed at 10° C. to 40° C.;
the duration for crystallization ranges from 8 to 72 hours;
the mass-volume ratio of ribociclib to the solvent ranges from 10 mg/mL to 50 mg/mL; and
the mass-volume ratio of orotic acid to the solvent ranges from 10 mg/mL to 65 mg/mL;

(2) the method is a solid grinding method;
the solvent is selected from the group consisting of methanol, ethanol, tetrahydrofuran, dichloromethane, water and any combination thereof;
the mass-volume ratio of ribociclib and orotic acid, to the solvent ranges from 27 mg/mL to 100 mg/mL; and
the solid grinding method is performed at 10° C. to 40° C.;

(3) the method is a volatilization method;
the solvent is selected from the group consisting of methanol, ethanol, isopropanol, ethyl acetate, acetonitrile, water and any combination thereof;
the volatilization method is performed at 10° C. to 40° C.; and
the mass-volume ratio of ribociclib and orotic acid, to the solvent ranges from 3 mg/mL to 20 mg/mL; or (4) the method is a cooling crystallization method;
the molar ratio of ribociclib to orotic acid ranges from 1:1 to 1:2;
the solvent is selected from the group consisting of methanol, ethanol, acetone, 1,4-dioxane, water and any combination thereof;
the crystallization temperature is from 0° C. to 30° C.;
the cooling rate ranges from 5 to 10° C./hour; and
the mass-volume ratio of ribociclib and orotic acid, to the solvent ranges from 19 mg/mL to 60 mg/mL.

19. A co-crystal of ribociclib monosuccinate and citric acid with the following formula (IV),

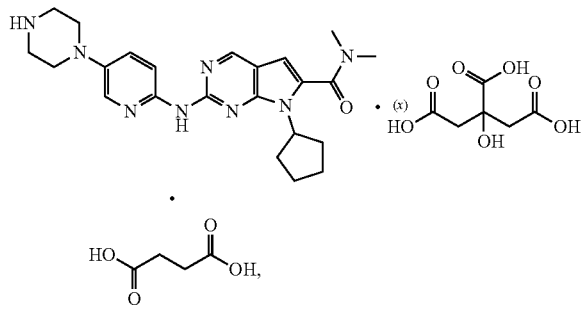

wherein x is 1; and wherein the co-crystal is in a crystalline form of an anhydrate, a hydrate, or a non-solvate.

20. The co-crystal of ribociclib monosuccinate and citric acid according to claim 19, wherein the crystalline form is a co-crystal form of ribociclib monosuccinate and citric acid.

21. The co-crystal form of ribociclib monosuccinate and citric acid according to claim 20, wherein the X-ray powder diffraction pattern of the co-crystal form, expressed as 2θ angles, has one or more of the following characteristic peaks:
8.4°±0.2°, 10.6°±0.2°, 12.9°±0.2° and 17.4°±0.2°.

22. The co-crystal form of ribociclib monosuccinate and citric acid according to claim 21, wherein the X-ray powder diffraction pattern of the co-crystal form, expressed as 2θ angles, has one or more of the following additional characteristic peaks: 4.3°±0.2°, 15.1°±0.2°, 18.8°±0.2°, 20.7°±0.2° and 22.2±0.2°.

23. The co-crystal form of ribociclib monosuccinate and citric acid according to claim 22, wherein the X-ray powder diffraction pattern of the co-crystal form, expressed as 2θ angles, has one or more of the following additional characteristic peaks: 12.3°±0.2°, 14.0°±0.2°, 16.8°±0.2°, 22.6°±0.2° and 23.8°±0.2°.

24. The co-crystal form of ribociclib monosuccinate and citric acid according to claim 23, wherein the X-ray powder diffraction pattern of the co-crystal form, expressed as 2θ angles, has one or more of the following additional characteristic peaks: 15.4°±0.2°, 15.9°±0.2°, 19.6°±0.2°, 21.6°±0.2° and 23.2°±0.2°.

25. A pharmaceutical composition comprising a therapeutically effective amount of the co-crystal of ribociclib monosuccinate and citric acid according to claim 19 and at least one pharmaceutically acceptable carrier.

26. A method of preparing the co-crystal of ribociclib monosuccinate and citric acid according to claim 19, the method comprising reacting ribociclib monosuccinate with one molar equivalent to two molar equivalents of citric acid, wherein the reacting is in an organic solvent or in combined organic solvents; and wherein the organic solvent is a solvent capable of dissolving ribociclib monosuccinate or citric acid.

27. A method of preparing the co-crystal of ribociclib monosuccinate and citric acid according to claim 19, the method comprising:
mixing ribociclib monosuccinate, citric acid, and a solvent, and removing the solvent after reaction to obtain the co-crystal of ribociclib monosuccinate and citric acid; wherein the solvent is selected from the group consisting of methanol, ethanol, isopropanol, ethyl acetate, dichloromethane, tetrahydrofuran, 1,4-dioxane, acetone, acetonitrile, dimethylsulfoxide, water, and any combination thereof; wherein:
(1) the method is a volatilization method;
the molar ratio of ribociclib monosuccinate to citric acid is 1:1;
the solvent is selected from the group consisting of methanol, ethanol, isopropanol, tetrahydrofuran, water and any combination thereof;
the volatilization method is performed at 10° C. to 40° C.; and
the mass-volume ratio of ribociclib monosuccinate and citric acid, to the solvent ranges from 1 mg/mL to 35 mg/mL;
(2) the method is a slurry method;
the molar ratio of ribociclib monosuccinate to citric acid ranges from 1:1 to 1:2;
the solvent is selected from the group consisting of methanol, ethanol, acetone, ethyl acetate, water, tetrahydrofuran and any combination thereof;
the slurry method is performed at 10° C. to 40° C.;
the duration for reaction ranges from 8 to 72 hours; and
the mass-volume ratio of ribociclib monosuccinate to the solvent ranges from 20 mg/mL to 50 mg/mL;
(3) the method is a solid grinding method;
the molar ratio of ribociclib monosuccinate to citric acid ranges from 1:0.5 to 1:2;
the solvent is selected from the group consisting of methanol, ethanol, acetone, tetrahydrofuran, dichloromethane and any combination thereof;
the mass-volume ratio of ribociclib monosuccinate and citric acid, to the solvent ranges from 50 mg/mL to 100 mg/mL; and
the solid grinding method is performed at 10° C. to 40° C.; or
(4) the method is a cooling crystallization method;
the starting point temperature ranges from 50° C. to 60° C.;
the molar ratio of ribociclib monosuccinate to citric acid ranges from 1:1 to 1:2;
the solvent is selected from the group consisting of methanol, ethanol, acetone, water, tetrahydrofuran, dimethyl sulfoxide and any combination thereof;
the ending point temperature is from 0° C. to 30° C.;
the cooling rate ranges from 5 to 10° C./hour; and
the mass-volume ratio of ribociclib monosuccinate to the solvent ranges from 10 mg/mL to 50 mg/mL.

* * * * *